United States Patent
You et al.

(10) Patent No.: US 10,442,759 B2
(45) Date of Patent: Oct. 15, 2019

(54) 1-SULFONAMIDO-4-ARYLOXY COMPOUNDS, AND PREPARATION METHOD AND MEDICINAL APPLICATION THEREOF

(71) Applicant: CHINA PHARMACEUTICAL UNIVERSITY, Nanjing (CN)

(72) Inventors: Qidong You, Nanjing (CN); Zhengyu Jiang, Nanjing (CN); Mengchen Lu, Nanjing (CN); Zhiyun Chen, Nanjing (CN); Haopeng Sun, Nanjing (CN); Xiaojin Zhang, Nanjing (CN); Xiaoke Guo, Nanjing (CN); Xiaoli Xu, Nanjing (CN)

(73) Assignee: CHINA PHARMACEUTICAL UNIVERSITY, Nanjing (CN)

( * ) Notice: Subject to any disclaimer, the term of this patent is extended or adjusted under 35 U.S.C. 154(b) by 0 days.

(21) Appl. No.: 15/755,356

(22) PCT Filed: Nov. 25, 2016

(86) PCT No.: PCT/CN2016/107350
§ 371 (c)(1),
(2) Date: Feb. 26, 2018

(87) PCT Pub. No.: WO2017/124835
PCT Pub. Date: Jul. 27, 2017

(65) Prior Publication Data
US 2018/0251423 A1     Sep. 6, 2018

(30) Foreign Application Priority Data
Jan. 18, 2016   (CN) .......................... 2016 1 0032080

(51) Int. Cl.
C07C 311/21    (2006.01)
C07C 303/38    (2006.01)
C07C 311/29    (2006.01)
C07D 257/04    (2006.01)
A61P 9/10      (2006.01)
A61P 25/28     (2006.01)
A61P 3/10      (2006.01)
A61P 11/00     (2006.01)
A61P 25/16     (2006.01)
C07C 303/08    (2006.01)
C07C 311/46    (2006.01)

(52) U.S. Cl.
CPC .............. *C07C 311/21* (2013.01); *A61P 3/10* (2018.01); *A61P 9/10* (2018.01); *A61P 11/00* (2018.01); *A61P 25/16* (2018.01); *A61P 25/28* (2018.01); *C07C 303/08* (2013.01); *C07C 303/38* (2013.01); *C07C 311/29* (2013.01); *C07C 311/46* (2013.01); *C07D 257/04* (2013.01)

(58) Field of Classification Search
CPC .................................................... C07C 311/21
See application file for complete search history.

(56) References Cited

U.S. PATENT DOCUMENTS

| | | |
|---|---|---|
| 2016/0083388 A1 | 3/2016 | Batist et al. |
| 2016/0090366 A1 | 3/2016 | Reddy |
| 2016/0318917 A1 | 11/2016 | Boehm et al. |

FOREIGN PATENT DOCUMENTS

| | | |
|---|---|---|
| CN | 105566241 A | 5/2016 |
| WO | WO 2011/156889 A1 | 12/2011 |
| WO | WO 2014/052889 A1 | 4/2014 |
| WO | WO 2014/183068 A2 | 11/2014 |
| WO | WO 2015/092713 A1 | 6/2015 |

OTHER PUBLICATIONS

Taha et al. Functional Foods in Health and Disease 2014; 4(11):510-523 p. 510. (Year: 2014).*

(Continued)

*Primary Examiner* — Emily A Bernhardt
(74) *Attorney, Agent, or Firm* — Buchanan Ingersoll & Rooney PC

(57) ABSTRACT

Compounds of formula (I) having 1-sulfonamido-4-aryloxy as a basic backbone. A preliminary activity test showed that the compounds provide excellent interference of a binding of Nrf2 by Keap1, thereby activating Nrf2. The compounds have a potential anti-inflammatory activity and can be used to treat a plurality of inflammation-associated diseases, including chronic obstructive pulmonary disease (COPD), Alzheimer's disease, Parkinson's disease, atherosclerosis, chronic kidney disease (CKD), diabetes, gastroenteritis, rheumatoid arthritis, and the like.

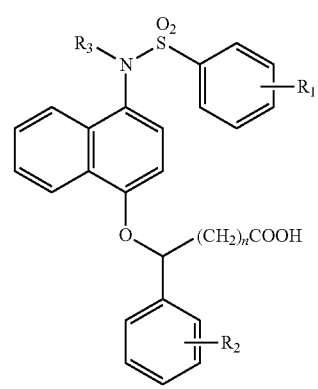

11 Claims, No Drawings

(56) References Cited

OTHER PUBLICATIONS

Gazaryan et al. Neural Regen Res. Nov. 2016; 11(11): 1708-1711. (Year: 2016).*
English Translation of the Written Opinion of the International Searching Authority (Form PCT/ISA/237) dated Feb. 27, 2017 by the State Intellectual Property Office of People's Republic of China in corresponding International Application No. PCT/CN2016/107350. (4 pages).
International Search Report (PCT/ISA/210) dated Feb. 27, 2017, by the State Intellectual Property Office of China as the International Searching Authority for International Application No. PCT/CN2016/107350.
Written Opinion (PCT/ISA/237) dated Feb. 27, 2017, by the State Intellectual Property Office of China as the International Searching Authority for International Application No. PCT/CN2016/107350.
Hayes et al., "NRF2 and KEAP1 mutations: permanent activation of an adaptive response in cancer", Trends Biochem Sci., Apr. 2009, 34(4), pp. 176-188, Abstract.
Kensler et al., "Cell survival responses to environmental stresses via the Keap1-Nrf2-ARE pathway", Annu Rev Pharmacol Toxicol, 2007, 47:89-116, Abstract.
Lee et al., "An Important Role of Nrf2-ARE Pathway in the Cellular Defense Mechanism", Journal of biochemistry and molecular biology 37(2): 139-43, Apr. 2004, Abstract.
Taguchi et al., "Molecular mechanisms of the Keap1-Nrf2 pathway in stress response and cancer evolution", Genes Cells, Feb. 2011, 16(2):123-40, Abstract.

* cited by examiner

1-SULFONAMIDO-4-ARYLOXY COMPOUNDS, AND PREPARATION METHOD AND MEDICINAL APPLICATION THEREOF

FIELD OF THE INVENTION

The present invention relates to the technical field of pharmaceutical chemistry, and particularly to compounds having 1-sulfonamido-4-aryloxy as a basic backbone which have anti-inflammatory activity, and preparation method and use thereof in anti-inflammatory area.

DESCRIPTION OF RELATED ART

At present, the anti-inflammatory drugs commonly used mainly include steroidal anti-inflammatory drugs, mainly including corticosteroids; and non-steroidal anti-inflammatory drugs, mainly including cyclooxygenase inhibitors. Although the chemical structures of non-steroidal anti-inflammatory drugs vary from one another, most of the non-steroidal anti-inflammatory drugs exert their anti-pyretic, analgesic, and anti-inflammatory effects through the inhibition of prostaglandin synthesis. All of these anti-inflammatory drugs currently used in clinic produce an anti-inflammatory effect by inhibiting the inflammatory reaction and cannot or rarely can improve the etiology of inflammation. The radical treatment of inflammation requires improving the microenvironment in which inflammation is formed and activating the in-vivo anti-inflammatory system. Inflammatory reaction has an important internal correlation with oxidative stress. Oxidative stress may lead to the damage of protein, nucleic acid and lipid molecules, thus causing inflammatory damage, activating inflammatory cytokines, and inducing and exacerbating the inflammatory reaction. The inflammation is closely related to the occurrence and development of tumors, cardiovascular diseases, Parkinson's disease, Alzheimer's disease, chronic nephropathy and other diseases. Proteins against oxidative stress can clear up reactive oxygen species, accelerate the metabolism of foreign matters, and increase the in vivo level of antioxidant proteins, and thus are effective in the treatment of inflammations by improving the inflammatory microenvironment (Trends Biochem Sci 2009; 34(4):176-188; Annu Rev Pharmacol Toxicol 2007; 47:89-116; J Biochem Mol Biol 2004; 37(2): 139-143; Genes Cells 2011; 16(2): 123-140).

Nrf2 was initially identified in heme-induced erythroid K562 cells in 1994, which is a key transcription factor involved in the regulation of oxidative stress. Nrf2 belongs to the leucine zipper nuclear transcription factor family and is homologous to the Cap n' Collar (CNC) family of *Drosophila melanogaster*. Human Nrf2 is highly homologous to the nuclear factor-erythroid 2 subunit p45. Most of the antioxidant genes associated with oxidative stress include an antioxidant response element (ARE), and Nrf2 exerts its transcription initiation activity by binding to ARE. The consensus sequence of AREs is 5'-RTGAYnnnGCR-3' (where R=A or G, Y=C or T). Keap1 is a main negative regulatory protein of Nrf2 in cells, which mainly functions to keep a low intracellular level of Nrf2 in normal cases; and the negative regulation of Nrf2 by Keap1 is relieved under stress to increase the Nrf2 level. Inhibition of the negative regulation of Nrf2 by Keap1 can effectively increase the Nrf2 level, activate the in vivo antioxidant system, reduce the inflammatory damage, and improve the inflammatory microenvironment, so as to achieve the effect of radical relief and treatment of inflammation.

Currently, Nrf2 activators are used to treat inflammatory-related diseases. For example, dimethyl fumarate has been approved by the FDA for use in the treatment of multiple sclerosis, and CDDO-Me is under Phase II clinical trial for the treatment of pulmonary hypertension (PAH). Other natural products and natural product-like compounds with anti-inflammatory activity have also been shown to activate Nrf2, such as curcumin, resveratrol and chalcone.

These Nrf2 activators mostly have a multi-unsaturated structure capable of binding to the thiol group in Keap1 and are deemed as covalent modification-type Nrf2 activators. Recently, it has been reported in the literatures that competitive interference with the Keap1-Nrf2 interaction can effectively relieve the negative regulation of Nrf2 by Keap1, so as to activate Nrf2. This approach to Nrf2 activation is competitive, specific, reversible and highly selective, by which the potential toxicity occurred in activation of Nrf2 by covalent modification is avoided, thus becoming currently a hot point in the study of drugs for treating inflammatory diseases by activation of Nrf2.

SUMMARY OF THE DISCLOSURE

The present disclosure describes compounds having an ether bond and a monosulfonamide structure, and a preparation method and pharmaceutical use thereof. A preliminary activity test shows that the compounds of the present disclosure provides excellent interference of a binding of Nrf2 by Keap1, thereby activating Nrf2. The compounds have a potential anti-inflammatory activity and can be used to treat a plurality of inflammation-associated diseases, including chronic obstructive pulmonary disease (COPD), Alzheimer's disease, Parkinson's disease, atherosclerosis, chronic kidney disease (CKD), diabetes, gastroenteritis, rheumatoid arthritis, and the like.

The compounds of the present disclosure have a structural Formula (I) below:

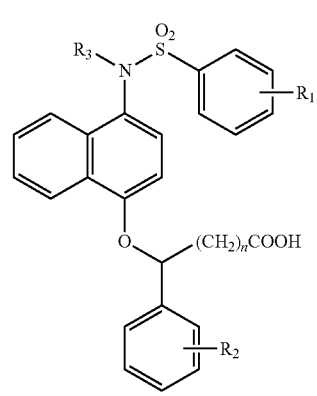

$R_1$ represents 4-trifluoromethyl, 4-trifluoromethoxy, 4-nitro, 4-hydroxyl, 4-hydroxymethyl, 4-cyano, 4-amino, H, halo, C1-C3 alkyl, C1-C3 alkoxy, C1-C3 alkylamino, or C1-C3 amido, at occurrence of mono-, di-, or tri-substitution;

$R_2$ represents 4-trifluoromethyl, 4-trifluoromethoxy, 4-nitro, 4-hydroxyl, 4-hydroxymethyl, 4-cyano, 4-amino, 4-morpholinylmethoxy, 4-benzylmethoxy, 4-benzylethoxy, H, halo, C1-C3 alkyl, C1-C3 alkoxy, C1-C3 alkylamino, or C1-C3 amido, at occurrence of mono-, di-, or tri-substitution;

R$_3$ represents H, —CH$_2$COOH,

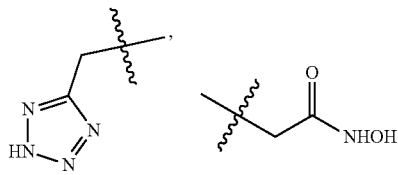

or —CH$_2$CONH$_2$; and n is 0-3.

R$_1$ preferably represents 4-methoxy, 4-bromo, 4-chloro, 4-fluoro, 2,4,6-trimethyl, 4-tert-butyl, 2,4,6-trimethoxy, 4-methyl, 3,4-dimethoxy, 4-acetamido, or 4-trifluoromethyl.

R$_2$ preferably represents 4-methoxy, 4-ethoxy, 4-isopropoxy, 4-fluoro, 4-chloro, 4-bromo, 4-acetamido, 4-trifluoromethyl, 4-hydroxyl, 4-morpholinylmethoxy, 4-morpholinylethoxy, 4-amino, or 4-benzylamino.

R$_3$ preferably represents —CH$_2$COOH or

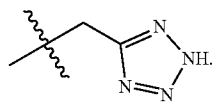 [SMILES: *Cc1nn[nH]n1]

n preferably represents 0 or 1.

Pharmaceutically acceptable salts thereof are preferably the sodium, potassium or calcium carboxylates of the compound of general Formula (I).

The present disclosure further describes a method for preparing the compounds general Formula (I). When R$_3$ is CH$_2$COOH, H, or

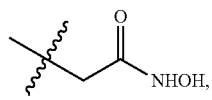

the preparation method is preferably as follows:

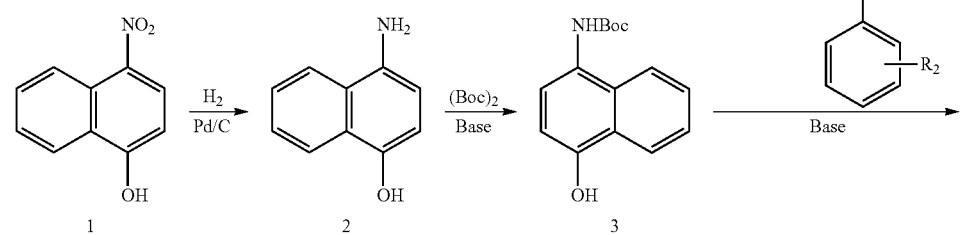

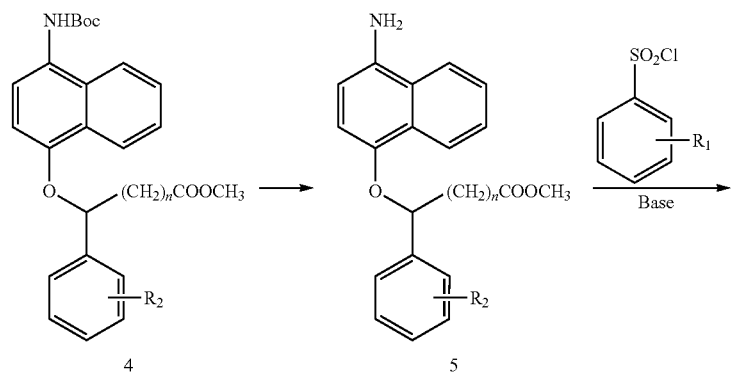

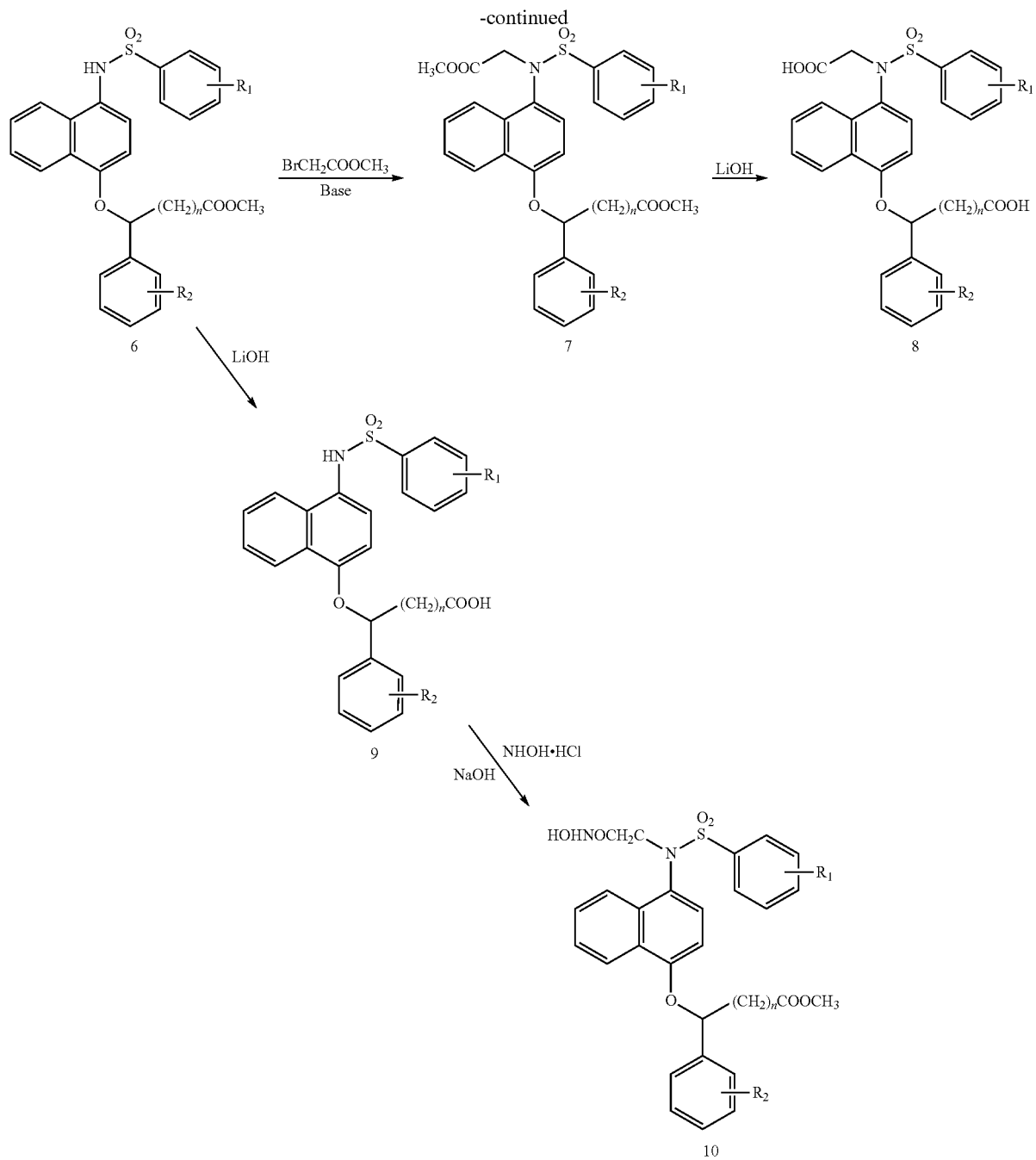

where $R_1$, $R_2$, and n are as defined above.

In the synthesis step of Compound (2) from Compound (1), reduction with hydrogen on palladium on carbon is employed, in which the solvent used is preferably methanol or tetrahydrofuran, and the palladium on carbon is preferably added in an amount of 10% mol. In the synthesis step of Compound (3) from Compound (2), the molar ratio of Compound (2) to the reactant $(Boc)_2O$ is preferably 1:1.5-1:2.

In the synthesis step of Compound (4) from Compound (3), the base used is preferably potassium bicarbonate, potassium carbonate, cesium carbonate, sodium carbonate, or sodium bicarbonate, and the solvent is preferably one or more of dimethyl sulfoxide (DMSO), N,N-dimethylformamide (DMF), 1,4-dioxane, and acetonitrile.

In the synthesis step of Compound (5) from Compound (4), the solvent system is preferably $HCl/CH_2Cl_2$ mixture, or $CF_3COOH/CH_2Cl_2$.

In the synthesis step of Compound (6) from Compound (5), the base used is preferably potassium carbonate, potassium bicarbonate, sodium carbonate, sodium bicarbonate, pyridine, or triethylamine, and the reaction is preferably carried out in a solvent such as tetrahydrofuran (THF), dichloromethane, or 1,4-dioxane.

In the synthesis step of Compound (7) from Compound (6), the weight ratio of Compound (6) to methyl bromoacetate is preferably 1:2-1:3, the base used is preferably potassium carbonate, potassium bicarbonate, sodium carbonate, sodium bicarbonate, pyridine, or triethylamine, the reaction is preferably carried out in a solvent such as dimethyl sulfoxide, N,N-dimethylformamide, 1,4-dioxane, or acetonitrile, and the reaction temperature is room temperature.

In the synthesis step of Compound (8) from Compound (7), lithium hydroxide is preferably added in such an amount that the concentration of lithium hydroxide in the solution is 1-3 mol/L, the solvent system is methanol/water system or ethanol/water system, and the reaction temperature is room temperature.

In the synthesis step of Compound (9) from Compound (6), lithium hydroxide is preferably added in such an amount that the concentration of lithium hydroxide in the solution is 1-3 mol/L, the solvent system is methanol/water system or ethanol/water system, and the reaction temperature is room temperature.

In the synthesis step of Compound (10) from Compound (7), lithium hydroxide is preferably added in such an amount that the concentration of lithium hydroxide in the solution is 1-3 mol/L, the solvent system is methanol/water system or ethanol/water system, and the reaction temperature is room temperature.

When $R_3$ is

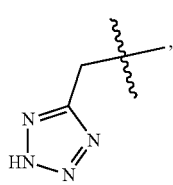

the preparation method is preferably as follows:

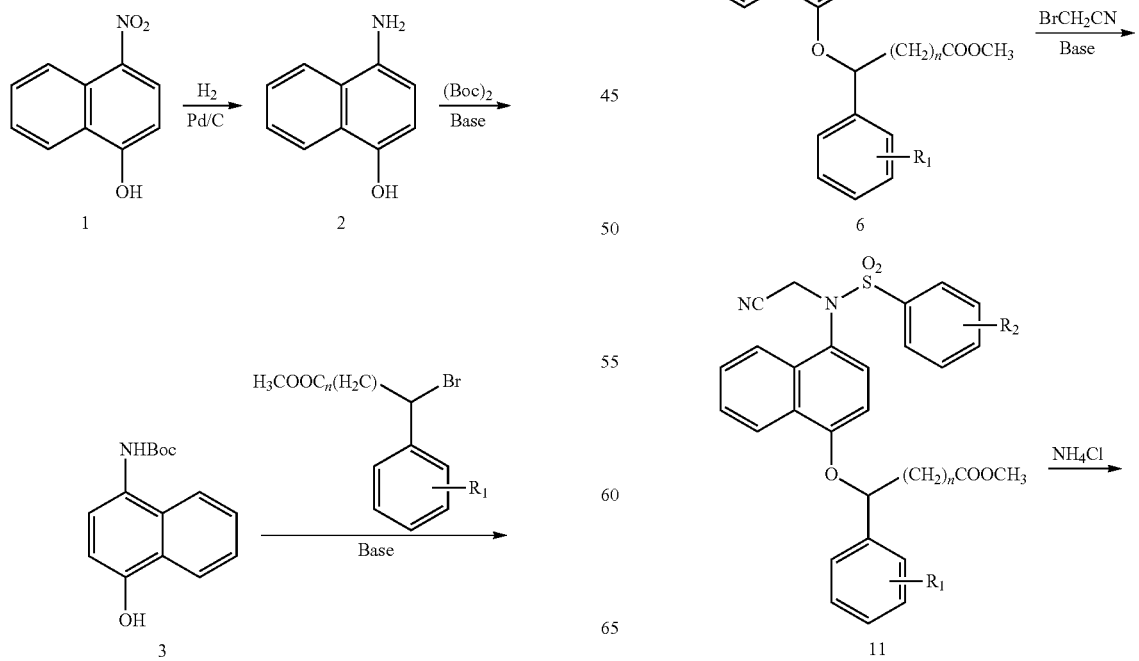

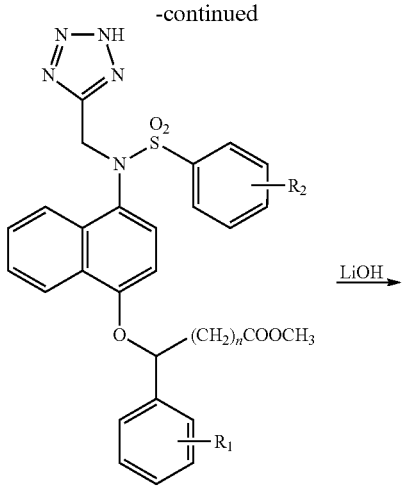

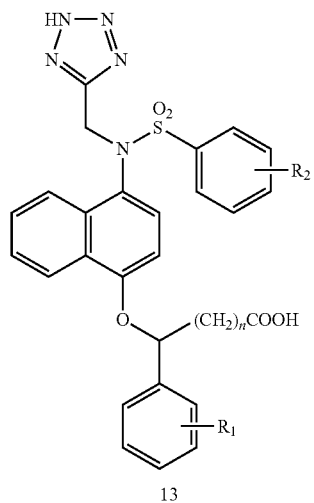

12

13 where $R_1$, $R_2$, and n are as defined above.

The synthesis procedure from Compound 1 through Compound 6 is the same as that when $R_3$ in the general Formula (I) is $CH_2COOH$ or H.

In the synthesis step of Compound 11 from Compound 6, the base used is preferably potassium carbonate, potassium bicarbonate, sodium carbonate, or sodium bicarbonate, the reaction is preferably carried out in a solvent such as dimethyl sulfoxide, N,N-dimethylformamide, 1,4-dioxane, or acetonitrile, the feed ratio (molar ratio) of Compound 6 to bromoacetonitrile is 1:1-1:4, and the reaction temperature is room temperature.

In the synthesis step of Compound 12 from Compound 11, the feed ratio (molar ratio) of Compound 11 to ammonium chloride is 1:4-1:8, the reaction is preferably carried out in a solvent such as N,N-dimethylformamide, 1,4-dioxane, or a combination thereof, and the reaction is carried out by heating to reflux.

In the synthesis step of target Compound (13) from Compound 12, lithium hydroxide is preferably added in such an amount that the concentration of lithium hydroxide in the solution is 1-3 mol/L, the solvent system is methanol/water system or ethanol/water system, and the reaction temperature is room temperature.

Preferred are the following compounds:

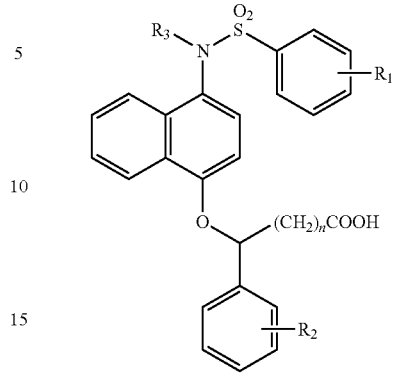

I

| No. | $R_1$ | $R_2$ | $R_3$ | n |
|---|---|---|---|---|
| I-1 | 4-$OCH_3$ | —H | —$CH_2COOH$ | 0 |
| I-2 | 2,4,6-$CH_3$ | —H | —$CH_2CONH_2$ | 0 |
| I-3 | 2,4,6-$CH_3$ | —H | —$CH_2COOH$ | 0 |
| I-4 | 4-$C(CH_3)_3$ | —H | —$CH_2COOH$ | 0 |
| I-5 | 3,4-$OCH_3$ | —H | —$CH_2COOH$ | 0 |
| I-6 | 2,4,6-$OCH_3$ | —H | —$CH_2COOH$ | 0 |
| I-7 | 4-$NHCOCH_3$ | —H | —$CH_2COOH$ | 0 |
| I-8 | 4-$NO_2$ | —H | —$CH_2COOH$ | 0 |
| I-9 | 4-F | —H | —$CH_2COOH$ | 0 |
| I-10 | 4-$CF_3$ | —H | —$CH_2COOH$ | 0 |
| I-11 | 2,4,6-$CH_3$ | —H | —H | 0 |
| I-12 | 2,4,6-$CH_3$ | —H | ![tetrazole-CH2] | 0 |
| I-13 | 2,4,6-$CH_3$ | —H | —$CH_2CONHOH$ | 0 |
| I-14 | 2,4,6-$CH_3$ | —$OCH_3$ | —$CH_2COOH$ | 0 |
| I-15 | 2,4,6-$CH_3$ | —$OCH_2CH_3$ | —$CH_2COOH$ | 0 |
| I-16 | 2,4,6-$CH_3$ | —$NHCOCH_3$ | —$CH_2COOH$ | 0 |
| I-17 | 2,4,6-$CH_3$ | —$OCH(CH_3)_2$ | —$CH_2COOH$ | 0 |
| I-18 | 2,4,6-$CH_3$ | —F | —$CH_2COOH$ | 0 |
| I-19 | 2,4,6-$CH_3$ | —$OCH_3$ | ![tetrazole-CH2] | 0 |
| I-20 | 2,4,6-$CH_3$ | —$OCH_3$ | —$CH_2COOH$ | 1 |

The compound numbers involved in the following pharmacological experiments are the compounds corresponding to the numbers here.

Based on the Nrf2-Keap1 protein-protein interaction, the present inventors have found novel active molecules with better physicochemical properties, which show, in a fluorescence polarization-based Keap1-Nrf2 protein-protein interaction inhibition experiment, an activity that is significantly better than a generally accepted positive control, a Nrf2 (Ac-LDEETGEFL-OH) polypeptide having 9 amino acids. In a luciferase reporter assay, the molecules show an induction activity superior to the positive control tBHQ (t-butylhydroquinone) and are expected to be further developed as an anti-inflammatory drug.

The pharmacological tests and results of some representative compounds of the present disclosure are shown below.

1. Fluorescence Polarization-Based Keap1-Nrf2 Protein-Protein Interaction Inhibition Experiment (FP Experiment)

The instrument used in the FP experiment was the SpectraMax Multi-Mode Microplate Reader (Molecular Devices), and the excitation and emission wavelengths of the instrument were selected based on the corresponding fluorophore. The experiment was performed using a Corning 3676 384 well plate. The reaction system in the plate was 40 μL containing 10 μL of 4 nM FITC-9mer Nrf2 polypeptide fluorescent probe, 10 μL of 12 nM Keap1 Kelch domain protein solution and 20 μL of a corresponding concentration of an inhibitor.

The positive control was 20 μL of 100 nM CPUY192002+ 10 μL probe+10 μL protein solution, the negative control was 10 μL probe+10 μL protein solution+20 μL HEPES buffer, and the blank control was 10 μL probe+30 μL HEPES buffer. Before the test, the system was mixed well and incubated for 30 minutes at room temperature. In this experiment, the probe fluorophore was fluorescein having an excitation wavelength of 485 nm and an emission wavelength of 535 nm. In this study, the fluorescence intensities in horizontal and vertical directions (F∥ and $F^{\perp}$) were used to calculate the millipolarization value (mP), so as to reflect the changes of the polarized light.

The inhibition rate of the inhibitor at a concentration is calculated by an equation below:

$$\text{Inhibition \%} = (1-(P_{obs}-P_{min})/(P_{max}-P_{min})) \times 100$$

where $P_{max}$, $P_{min}$, and $P_{obs}$ represent the polarization value in the well containing Keap1 and the fluorescence probe, the polarization value in the well containing the fluorescence probe, and the polarization value of the well containing the inhibitor, respectively. The $IC_{50}$ of the compounds was calculated from curve of the inhibition rate against the inhibitor concentration.

| Compound No. | $IC_{50}$ (μM) |
| --- | --- |
| I-1 | 2.28 |
| I-2 | 1.32 |
| I-3 | 0.58 |
| I-4 | 0.98 |
| I-5 | 2.30 |
| I-6 | 0.64 |
| I-7 | 5.23 |
| I-8 | 4.79 |
| I-9 | 5.16 |
| I-10 | 6.66 |
| I-11 | 2.43 |
| I-12 | 0.83 |
| I-13 | 0.98 |
| I-14 | 0.081 |
| I-15 | 0.084 |
| I-16 | 0.090 |
| I-17 | 0.320 |
| I-18 | 0.31 |
| I-19 | 0.140 |
| I-20 | 0.83 |
| Nrf2 9mer Peptide (Ac-LDEETGEFL-OH) | 0.33 |

As can be seen from the above table, Compounds I-14, 15, and 16 are shown to be better than the positive control, a Nrf2 polypeptide comprising 9 amino acids.

2. ARE Luciferase Reporter Assay

In Vitro Cell Culture

HepG2 cells transfected with the ARE luciferase reporter plasmid (obtained by transfecting with the Antioxidant Response Reporter plasmid purchased from QIAGEN following the manufacturer's instruction) were cultured in a RPMI-1640 medium containing 10% fetal bovine serum at 37° C. and 5% $CO_2$.

(1) HepG2-ARE-C8 cells in logarithmic growth phase were treated with a 0.25% trypsin digestion solution to prepare a cell suspension with a concentration of $4 \times 10^5$ cells/μL. 100 μL was added to a 96-well microtiter plate and incubated overnight.

(2) 2 times of the desired concentration of the test compound was formulated in a culture medium, and 100 μL was added respectively to the corresponding wells. tBHQ was used as a positive control and DMSO was used as a negative control. The 96-well microtiter plate added with the compound was incubated for 12 hrs at a constant temperature of 37° C., 5% $CO_2$, and saturated humidity.

(3) The 5× lysis buffer in the Luciferase Assay Kit was formulated into a 1× lysis buffer for future use.

(4) The 96-well microtiter plate was removed, the medium was aspirated from the wells, the cells were washed with 1×PBS buffer, and the PBS buffer was aspirated off after the wash. 25 or 30 μL of the 1× cell lysis buffer was added to each well and the cells were lysed on ice for 15 min. After the lysis, the lysate was stood for 3-5 min, and 20 μL of the lysate supernatant was aspirated into a corresponding 96-well white plate.

(5) The 96-well white plate was positioned in the Thermo Scientific Luminoskan Ascent Chemiluminescence Micropore Reader. 100 μL of a luciferase assay reagent (obtained by uniformly mixing 1 bottle of luciferase assay substrate in the luciferase assay kit and 1 bottle of luciferase detection buffer) was added to each well before the test, and the plate was read within 1 min after the test reagent was added.

| | Luciferase reporter activity (fold of induction) | | |
| --- | --- | --- | --- |
| Compound No. | 0.1 μmol/L | 1 μmol/L | 10 μmol/L |
| I-1 | 0.98 | 1.10 | 1.07 |
| I-2 | 1.21 | 1.10 | 1.05 |
| I-3 | 0.95 | 1.03 | 1.31 |
| I-4 | 1.04 | 1.12 | 1.13 |
| I-5 | 0.92 | 1.05 | 1.10 |
| I-6 | 1.01 | 1.26 | 1.09 |
| I-7 | 0.97 | 1.01 | 1.03 |
| I-8 | 1.05 | 1.23 | 1.14 |
| I-9 | 1.02 | 1.13 | 1.08 |
| I-10 | 0.92 | 0.95 | 1.10 |
| I-11 | 1.02 | 1.34 | 1.14 |
| I-12 | 1.05 | 1.19 | 1.36 |
| I-13 | 1.07 | 1.16 | 1.21 |
| I-14 | 1.13 | 2.31 | 5.75 |
| I-15 | 1.33 | 2.05 | 3.92 |
| I-16 | 1.21 | 1.98 | 3.23 |
| I-17 | 1.39 | 1.39 | 2.07 |
| I-18 | 1.03 | 1.42 | 1.57 |
| I-19 | 0.97 | 1.43 | 2.58 |
| I-20 | 1.02 | 1.13 | 1.28 |
| tBHQ (t-butylhydroquinone) | 1.46 | 1.38 | 3.61 |

As can be seen from the above table, most of the compounds cannot significantly activate ARE at a low concentration; however, in the FP assay, Compounds I-14 and I-15 with the most preferred IC50 are able to efficiently activate ARE at 10 μM, and the fold of induction is significantly higher than that of the positive control tBHQ. In addition, the molecules of the present disclosure have a novel structure and a good membrane permeability (Log P=4.28±0.45

(I-14), and 4.81±0.45 (I-15)), and are expected to be developed as an anti-inflammatory drug that can enter the brain by penetrating through the blood-brain barrier by take advantage of the Log P.

DETAILED DESCRIPTION OF THE DISCLOSURE

Example 1

2-(4-(N-(carboxymethyl)-4-methoxybenzenesulfonamido))naphthalen-1-oxy)benzene acetic acid (1) Tert-butyl 4-hydroxynaphthalen-1-carbamate (1-1)

1-Hydroxy-4-nitronaphthalene (2.8 g, 14.8 mmol) was dissolved in $CH_3OH$ (30 ml), and 5% palladium on carbon (157 mg, 1.48 mmol) was added. A hydrogen balloon was coupled, and the reaction was carried out at room temperature. After the reaction was complete by TLC, the palladium on carbon was filtered off. $(Boc)_2O$ (5.1 ml, 22.2 mmol) and triethylamine (4.1 ml, 29.6 mmol) were added to the filtrate, and reacted for 5 hrs at room temperature under $N_2$ atmosphere. After the reaction was complete by TLC, most of the methanol was removed by rotary evaporation. Water was added, and the mixture was extracted with ethyl acetate (EA) (20 ml×3). The organic layers were combined, washed with a saturated NaCl solution (10 ml×3), dried over anhydrous sodium sulfate, rotary evaporated to dryness, and slurried in dichloromethane, to obtain a grey solid (2.5 g). Yield: 65.1%, m.p.: 178.9-180.8° C. $^1$H-NMR (300 MHz, DMSO) δ 1.46 (s, 9H, -Boc), 6.80 (d, 1H, J=8.01 Hz, Ar—H), 7.20 (d, 1H, J=7.95 Hz, Ar—H) 7.42-7.52 (m, 2H, Ar—H), 7.84 (d, 1H, J=7.92 Hz, Ar—H), 8.12 (d, 1H, J=7.83 Hz, Ar—H), 8.83 (s, 1H, —NH—), 10.07 (s, 1H, —OH); EI-MS m/z: 260 $[M+H]^+$.

(2) Methyl 2-((4-tert-butoxycarbonylamino)naphthalen-1-oxy)-benzeneacetate (1-2)

Compound (1-1) (2.5 g, 9.6 mmol) was dissolved in DMF (10 ml), and potassium carbonate (2.7 g, 19.3 mmol) and then methyl bromobenzeneacetate (1.8 ml, 11.6 mmol) were added and stirred at room temperature. After the reaction was complete by TLC, water was added to the solution, adjusted to pH 7 with a saturated $NH_4Cl$ solution, and extracted with EA (20 ml×3). The organic layers were combined, washed with a saturated NaCl solution (3×), directly powdered, and separated by column chromatography (petroleum ether (PE):EA=10:1), to obtain a grey product (1.34 g). Yield: 34.1%, m.p. 198.8-200.5° C. $^1$H-NMR (300 MHz, DMSO) δ 1.46 (s, 9H, -Boc), 3.66 (s, 3H, —OCH$_3$), 6.24 (s, 1H, —OCH—), 6.90 (d, 1H, J=8.34 Hz, Ar—H), 7.31 (d, 1H, J=8.16 Hz, Ar—H), 7.40-7.46 (m, 3H, Ar—H), 7.56-7.58 (m, 2H, Ar—H), 7.66-7.68 (m, 2H, Ar—H), 7.91-7.94 (m, 1H, Ar—H), 8.29-8.32 (m, 1H, Ar—H) 9.00 (s, 1H, —NH); EI-MS m/z: 430 $[M+Na]^+$.

(3) Methyl 2-((4-(4-methoxybenzenesulfonamido) naphthalen-1-oxy)-benzeneacetate (1-3)

Compound (1-2) (500.0 mg, 1.2 mmol) was dissolved in $CH_2Cl_2$ (10.0 ml), and $CF_3COOH$ (5.0 ml, 67.3 mmol) was added and stirred at room temperature. After the reaction was complete by TLC (about 0.5 hr), the reaction solution was adjusted to pH 7 with a saturated $Na_2CO_3$ solution and extracted with EA (20 ml×3). The organic layers were combined, washed with a saturated sodium chloride solution (3×), dried over anhydrous sodium sulfate, and rotary evaporated to dryness, to obtain a grey solid 5, which was directly dissolved in THF without further treatment. p-Methoxyphenylsulfonyl chloride (322.0 mg, 1.5 mmol), and then pyridine (197.7 μL, 2.5 mmol) were added and stirred at room temperature. After the reaction was complete by TLC (about 8 hrs), THF was rotary evaporated to dryness, and a small amount of acetone was added to dissolve the oil. A dilute hydrochloric acid solution was added until the solution became cloudy, and then the solution was extracted with EA (20 ml×3). The organic layers were combined, directly powdered by rotary evaporation to dryness, and separated by column chromatography on silica gel (PE:EA=8:1), to obtain a pale purple solid (185.0 mg). Yield: 34.4%, m.p.: 223-225° C. $^1$H-NMR (300 MHz, DMSO) δ 3.64 (s, 3H, —COOCH$_3$), 3.76 (s, 3H, —OCH$_3$), 6.20 (s, 1H, —OCH—), 6.81 (d, 1H, J=8.43 Hz, Ar—H), 6.91-6.99 (m, 3H, Ar—H), 7.39-7.55 (m, 7H, Ar—H), 7.61-7.64 (m, 2H, Ar—H), 7.91-7.94 (m, 1H, Ar—H), 8.21-8.24 (m, 1H, Ar—H), 9.84 (s, 1H, —NH); EI-MS m/z: 500 $[M+Na]^+$.

(4) Methyl 2-(4-(4-methoxy-N-(methoxycarbonylmethyl)benzenesulfonamido) naphthalen-1-oxy)-benzeneacetate (1-4)

Compound (1-3) (185.0 mg, 387.0 μmol) was dissolved in DMF (5 ml), and potassium carbonate (107.0 mg, 775.0 μmol) and then methyl bromoacetate (54 μL, 581 μmol) were added and stirred at room temperature. After the reaction was complete by TLC (about 2 hrs), water was added to the solution until the solution became cloudy. The solution was adjusted to pH 7 with a saturated $NH_4Cl$ solution. A purple solid was precipitated out, which was suctioned and dried. 138.0 mg of the purple solid was obtained. Yield: 64.8%, m.p. 134-136° C. $^1$H-NMR (300 MHz, DMSO) δ 3.54-3.59 (m, 3H, —COOCH$_3$), 3.65-3.71 (m, 3H, —COOCH$_3$), 3.84-3.85 (m, 3H, —OCH$_3$), 4.43-4.55 (m, 2H, —NCH$_2$—), 6.26 (s, 1H, —OCH—), 6.85-6.87 (m, 1H, Ar—H), 7.03-7.09 (m, 3H, Ar—H), 7.42-7.50 (m, 3H, Ar—H), 7.69-7.58 (m, 6H, Ar—H), 7.99-8.01 (m, 1H, Ar—H), 8.27-8.28 (m, 1H, Ar—H); EI-MS m/z: 572 $[M+Na]^+$.

(5) 2-(4-(N-(carboxymethyl)-4-methoxybenzenesulfonamido))naphthalen-1-oxy) benzeneacetic acid (I-1)

Compound (1-4) (138.0 mg, 251.0 μmol) was dissolved in methanol (3 ml), and water (3 ml) and then LiOH (0.3 g, 12.5 mmol) were added, and stirred overnight at room temperature. After the reaction was complete by TLC (about 10 hrs), a small amount of water was added to the system until the solution became cloudy. The solution was adjusted to pH 4 with a hydrochloric acid solution. The solution became cloudy, and a purple solid was precipitated out, which was suctioned and dried. 105 mg of the purple solid was obtained. Yield: 80.2%, m.p. 226-228° C. $^1$H-NMR (300 MHz, DMSO) δ 3.83-3.85 (s, 3H, —OCH$_3$), 4.23-4.47 (m, 2H, —NCH$_2$—), 6.05 (s, 1H, —OCH—), 6.81-6.84 (m, 1H, Ar—H), 7.02-7.12 (m, 3H, Ar—H), 7.38-7.70 (m, 9H, Ar—H), 8.00-8.06 (m, 1H, Ar—H), 8.27-8.30 (m, 1H, Ar—H) 13.07 (br, 2H, —COOH); HRMS (ESI): calcd. for $C_{27}H_{23}NO_8S$. $[M+H]^+$ 522.1217, found 522.1225.

Example 2

2-(4-(N-(carboxymethyl)-4-(2-naphthylbenzenesulfonamido))naphthalen-1-oxy) benzeneacetic acid The synthesis method of Compound (1-2) was exactly the same as that in Example 1.

(1) Methyl 2-(4-(2,4,6-trimethylbenzenesulfonamido)naphthalen-1-oxy)-benzene acetate (2-1)

Compound (1-2) (2.2 g, 5.4 mmol) was dissolved in $CH_2Cl_2$ (10.0 ml), and $CF_3COOH$ (10.0 ml, 135.1 mmol) was added and stirred at room temperature. After the reaction was complete by TLC (about 0.5 hr), the reaction solution was adjusted to pH 7 with a saturated $Na_2CO_3$ solution and extracted with EA (20 ml×3). The organic layers were combined, washed with a saturated sodium chloride solution (3×), dried over anhydrous sodium sulfate, and rotary evaporated to dryness, to obtain a grey solid 5, which was directly dissolved in THF without further treatment. 2,4,6-Trimethylphenylsulfonyl chloride (1.4 g, 6.4 mmol) and then pyridine (648.0 μL, 8.1 mmol) were added and stirred at room temperature. After the reaction was complete by TLC (about 8 hrs), THF was rotary evaporated to dryness, and a small amount of acetone was added to dissolve the oil. A dilute hydrochloric acid solution was added until the solution became cloudy and then the solution was extracted with EA (20 ml×3). The organic layers were combined, directly powdered by rotary evaporation to dryness, and separated by column chromatography on silica gel (PE:EA=8:1), to obtain a pale purple solid (1.5 g). Yield: 54.9%, m.p. 213-215° C. $^1$H-NMR (300 MHz, $CDCl_3$) δ 2.30 (s, 3H, —C$\underline{H}_3$), 2.44 (s, 6H, —C$\underline{H}_3$), 3.74 (s, 3H, —COOC$\underline{H}_3$), 5.79 (s, 1H, —OC$\underline{H}$—), 6.51-6.54 (m, 1H, Ar—$\underline{H}$), 6.83-6.86 (m, 1H, Ar—$\underline{H}$), 6.90 (s, 2H, Ar—$\underline{H}$), 7.42-7.44 (m, 2H, Ar—$\underline{H}$), 7.52-7.56 (m, 3H, Ar—$\underline{H}$), 7.64-7.67 (m, 2H, Ar—$\underline{H}$), 7.97-8.00 (m, 1H, Ar—$\underline{H}$), 8.41-8.44 (m, 1H, Ar—$\underline{H}$); EI-MS m/z: 512 [M+Na]$^+$.

(2) Methyl 2-(4-(2,4,6-trimethylphenyl-N-(methoxycarbonylmethyl)sulfonamido) naphthalen-1-oxy)-benzeneacetate (2-2)

Compound (2-1) (200.0 mg, 409.0 μmol) was dissolved in DMF (5 ml), and potassium carbonate (85.0 mg, 613.0 μmol) and then bromoacetamide (68.0 mg, 490.0 μmol) were added and stirred at room temperature. After the reaction was complete by TLC (about 2 hrs), water was added to the solution until the solution became cloudy. The solution was adjusted to pH 7 with a saturated $NH_4Cl$ solution. A purple solid was precipitated out, which was suctioned and dried. 173 mg of the purple solid was obtained. Yield: 77.6%, m.p. 93.7-97.7° C. $^1$H-NMR (300 MHz, DMSO) δ 2.11 (s, 3H, —C$\underline{H}_3$), 2.19 (s, 6H, —C$\underline{H}_3$), 3.64-3.67 (s, 3H, —OC$\underline{H}_3$), 4.22-4.24 (m, 1H, —NC$\underline{H}_2$—), 4.52-4.54 (m, 1H, —NC$\underline{H}_2$—), 6.28-6.30 (m, 1H, —OC$\underline{H}$—), 6.82 (s, 2H, Ar—$\underline{H}$), 6.87-6.91 (m, 1H, Ar—$\underline{H}$), 7.35-7.38 (m, 1H, Ar—$\underline{H}$), 7.41-7.49 (m, 5H, Ar—$\underline{H}$), 7.64-7.66 (m, 2H, Ar—H), 7.78-7.82 (m, 1H, Ar—$\underline{H}$), 8.24-8.28 (m, 1H, Ar—$\underline{H}$); EI-MS m/z: 569.1712 [M+Na]$^+$.

(3) 2-(4-(2,4,6-trimethylbenzenesulfonamido)naphthalen-1-yl)oxy)-2-benzeneacetic acid (I-2)

Compound (2-2) (167.0 mg, 314.0 μmol) was dissolved in methanol (3 ml), and water (3 ml) and then LiOH (300.0 mg, 12.5 mmol) were added and stirred overnight at room temperature. After the reaction was complete by TLC (about 10 hrs), a small amount of water was added to the system until the solution became cloudy. The solution was adjusted to pH 4 with a hydrochloric acid solution. The solution became cloudy, and a purple solid was precipitated out, which was suctioned and dried, to obtain a pale pink solid (126.0 mg). Yield: 77.3%, m.p. 236-238° C. $^1$H-NMR (300 MHz, DMSO) δ 2.14 (s, 3H, —C$\underline{H}_3$), 2.17 (s, 3H, —C$\underline{H}_3$), 2.21 (s, 3H, —C$\underline{H}_3$), 4.13-4.23 (m, 1H, —NC$\underline{H}_2$—), 4.51-4.60 (m, 1H, —NC$\underline{H}_2$—), 5.90 (s, 1H, —OC$\underline{H}$—), 6.81-6.88 (m, 3H, Ar—$\underline{H}$), 6.92-6.96 (m, 1H, Ar—$\underline{H}$), 7.25-7.30 (m, 1H, Ar—$\underline{H}$), 7.34-7.50 (m, 6H, Ar—$\underline{H}$), 7.62-7.66 (m, 2H, Ar—$\underline{H}$), 7.75-7.79 (m, 1H, Ar—$\underline{H}$), 8.25-8.31 (m, 2H, Ar—$\underline{H}$); EI-MS HRMS (ESI): calcd. for $C_{30}H_{24}NO_7S$. [M–H]$^-$ 531.1590, found 531.1609.

Example 3

The synthesis method of Compound (2-1) was exactly the same as that in Example 2.

(1) Methyl 2-(4-((2,4,6-trimethyl)-N-(methoxycarbonylmethyl)benzenesulfonamido) naphthalen-1-oxy)-benzeneacetate (3-1)

Compound (2-1) (200.0 mg, 402.0 μmol) was dissolved in DMF (5 ml), potassium carbonate (113.0 mg, 817.0 μmol), and then methyl bromoacetate (56.8 μL, 612.8.0 μmol) were added and stirred at room temperature. After the reaction was complete by TLC (about 2 hrs), water was added to the solution, until the solution became cloudy. The solution was adjusted to pH 7 with a saturated $NH_4Cl$ solution, and a purple solid was precipitated out, which was suctioned and dried. 176 mg of the purple solid was obtained. Yield: 76.7%, m.p. 122-124° C. $^1$H-NMR (300 MHz, CDCl3) δ 2.21 (s, 3H, —C$\underline{H}_3$), 2.25 (s, 3H, —C$\underline{H}_3$), 2.29 (s, 3H, —C$\underline{H}_3$), 3.66-3.69 (m, 3H, —COOC$\underline{H}_3$), 3.75-3.76 (m, 3H, —COOC$\underline{H}_3$), 4.34-4.40 (m, 1H, —NC$\underline{H}_2$—), 4.88-4.97 (m, 1H, —NC$\underline{H}_2$—), 5.82-5.83 (s, 1H, —OC$\underline{H}$—), 6.59-6.63 (m, 1H, Ar—$\underline{H}$), 6.74-6.77 (m, 2H, Ar—$\underline{H}$), 7.40-7.57 (m, 6H, Ar—$\underline{H}$), 7.64-7.74 (m, 3H, Ar—$\underline{H}$), 8.40-8.43 (m, 1H, Ar—H); EI-MS m/z: 584 [M+Na]$^+$.

(3) 2-(4-(N-(carboxymethyl)-2,4,6-trimethylbenzenesulfonamido))naphthalen-1-oxy) benzeneacetic acid (I-3)

Compound (3-1) (176.0 mg, 313.4 μmol) was dissolved in methanol (5 ml), and water (5 ml) and then LiOH (500.0 mg, 20.8 mmol) were added, stirred overnight at room temperature. After the reaction was complete by TLC (about 10 hrs), a small amount of water was added to the system until the solution became cloudy. The solution was adjusted to pH 4 with a hydrochloric acid solution. The solution became cloudy, and a purple solid was precipitated out, which was suctioned and dried to obtain an off-white solid (105.0 mg). Yield: 62.8%, m.p. 213-215° C.

$^1$H-NMR (300 MHz, DMSO) δ 2.12-2.20 (m, 9H, —C$\underline{H}_3$), 4.28-4.38 (m, 1H, —NC$\underline{H}_2$—), 4.64-4.72 (m, 1H, —NC$\underline{H}_2$—), 6.11-6.14 (m, 1H, —OC$\underline{H}$—), 6.83-6.89 (m, 3H, Ar—$\underline{H}$), 7.42-7.48 (m, 5H, Ar—$\underline{H}$), 7.62-7.79 (m, 4H, Ar—$\underline{H}$), 8.27-8.29 (m, 2H, Ar—$\underline{H}$), 12.88 (br, 2H, —COOH); EI-MS HRMS (ESI): calcd. for $C_{29}H_{27}NO_7S$. [M+H]$^+$ 534.1505, found 534.1508.

Example 4

The synthesis method of Compound (1-2) was exactly the same as that in Example 1.

(1) Methyl 2-((4-(4-tert-butylbenzenesulfonamido) naphthalen-1-oxy)-benzeneacetate (4-1)

Compound (1-2) (995.0 mg, 2.4 mmol) was dissolved in $CH_2Cl_2$ (10.0 ml), $CF_3COOH$ (10.0 ml, 135.1 mmol) was added and stirred at room temperature. After the reaction was complete by TLC (about 0.5 hr), the reaction solution was adjusted to pH 7 with a saturated $Na_2CO_3$ solution and extracted with EA (20 ml×3). The organic layers were combined, washed with a saturated sodium chloride solution (3×), dried over anhydrous sodium sulfate, and rotary evaporated to dryness, to obtain a grey solid 5, which was directly dissolved in THF without further treatment. 4-tert-butylphenylsulfonyl chloride (681.0 mg, 2.9 mmol) and then pyridine (393.0 μL, 4.9 mmol) were added and stirred at room temperature. After the reaction was complete by TLC (about 8 hrs), THF was rotary evaporated to dryness, and a small amount of acetone was added to dissolve the oil. A dilute hydrochloric acid solution was added until the solution became cloudy and then the solution was extracted with EA (20 ml×3). The organic layers were combined, directly powdered by rotary evaporation to dryness, and separated by column chromatography on silica gel (PE:EA=8:1), to obtain a pale purple solid (738 mg). Yield: 60.0%, m.p. 220-222° C.

$^1$H-NMR (300 MHz, $CDCl_3$) δ 1.12-1.14 (m, 9H, —C$\underline{H}_3$), 3.69 (s, 3H, —COOC$\underline{H}_3$), 5.73 (s, 1H, —OCH—), 6.54-6.56 (m, 2H, Ar—$\underline{H}$), 7.15-7.20 (m, 3H, Ar—$\underline{H}$), 7.36-7.37 (m, 4H, Ar—$\underline{H}$), 7.51-7.60 (m, 5H, Ar—$\underline{H}$), 8.32-8.35 (m, 1H, Ar—$\underline{H}$); EI-MS m/z: 526 [M+Na]$^+$.

(2) Methyl 2-(4-(4-tert-butyl-N-(methoxycarbonylmethyl)benzenesulfonamido) naphthalen-1-oxy)-benzeneacetate (4-2)

Compound (4-1) (738.0 mg, 1.5 mmol) was dissolved in DMF (5 ml), and potassium carbonate (304.0 mg, 2.2 mmol) and then methyl bromoacetate (163.0 μL, 1.76 mmol) were added and stirred at room temperature. After the reaction was complete by TLC (about 2 hrs), water was added to the solution, until the solution became cloudy. The solution was adjusted to pH 7 with a saturated $NH_4Cl$ solution, and then extracted with EA (3×). The organic layers were combined, washed with a saturated sodium chloride solution (3×), powdered by rotary evaporation to dryness, and then separated and purified by column chromatography (PE:EA=4:1), to obtain a pale red product (239 mg). Yield: 28.3%, m.p. 108-110° C.

$^1$H-NMR (300 MHz, DMSO) δ 1.31-1.32 (m, 9H, —C$\underline{H}_3$), 3.55-3.60 (m, 3H, —COOC$\underline{H}_3$), 3.67-3.73 (m, 3H, —COOC$\underline{H}_3$), 4.33-4.45 (m, 1H, —NC$\underline{H}_2$—), 4.58-4.67 (m, 1H, —NC$\underline{H}_2$—), 6.30-6.31 (s, 1H, —OCH—), 6.88-6.90 (m, 1H, Ar—$\underline{H}$), 7.17-7.20 (m, 1H, Ar—$\underline{H}$), 7.44-7.59 (m, 9H, Ar—$\underline{H}$), 7.64-7.71 (m, 2H, Ar—$\underline{H}$), 7.76-7.87 (m, 1H, Ar—H) 8.24-8.30 (m, 1H, Ar—H); EI-MS m/z: 598 [M+Na]$^+$.

(3) 2-(4-(N-(carboxymethyl)-4-tert-butylbenzenesulfonamido))naphthalen-1-oxy) benzeneacetic acid (I-4)

Compound (4-2) (239.0 mg, 415 μmol) was dissolved in methanol (10 ml), and water (5 ml) and then LiOH (800.0 mg, 33.4 mmol) were added and stirred at room temperature. After the reaction was complete by TLC (about 10 hrs), a small amount of water was added to the system until the solid was completely dissolved. The solution was adjusted to pH 2 with a hydrochloric acid solution. The solution became cloudy, and a grey solid was precipitated out, which was stood, suctioned and dried. 349.0 mg of the grey solid was obtained. Yield: 81.9%, m.p. 189-195° C.

$^1$H-NMR (300 MHz, DMSO) δ 1.24-1.32 (m, 9H, —C$\underline{H}_3$), 4.25-4.26 (m, 1H, —NC$\underline{H}_2$—), 4.49-4.55 (m, 1H, —NC$\underline{H}_2$—), 6.12-6.13 (m, 1H, —OCH—), 6.87-6.89 (m, 1H, Ar—$\underline{H}$), 7.21-7.22 (m, 1H, Ar—$\underline{H}$), 7.44-7.58 (m, 9H, Ar—$\underline{H}$), 7.66-7.72 (m, 2H, Ar—$\underline{H}$), 7.76-7.89 (m, 1H, Ar—H), 8.29-8.31 (m, 1H, Ar—H), 12.98 (br, 2H, —COOH); EI-MS HRMS (ESI): calcd. for $C_{30}H_{30}NO_7S$. [M+H]$^+$ 548.1737, found 548.1743.

Example 5

The synthesis method of Compound (1-2) was exactly the same as that in Example 1.

(1) Methyl 2-((4-(3,4-dimethoxybenzenesulfonamido)naphthalen-1-oxy)-benzene acetate (5-1)

Compound (1-2) (500.0 mg, 1.2 mmol) was dissolved in $CH_2Cl_2$ (10.0 ml), and then $CF_3COOH$ (5.0 ml, 67.3 mmol) was added and stirred at room temperature. After the reaction was complete by TLC (about 0.5 hrs), the reaction solution was adjusted to pH 7 with a saturated $Na_2CO_3$ solution and extracted with EA (20 ml×3). The organic layers were combined, washed with a saturated sodium chloride solution (3×), dried over anhydrous sodium sulfate, and rotary evaporated to dryness, to obtain a grey solid 5, which was directly dissolved in THF without further treatment. 3,4-Dimethoxyphenylsulfonyl chloride (582.2 mg, 2.5 mmol) and then pyridine (198.1 μL, 2.46 mmol) were added and stirred at room temperature. After the reaction was complete by TLC (about 8 hrs), THF was rotary evaporated to dryness, and a small amount of acetone was added to dissolve the oil. A dilute hydrochloric acid solution was added until the solution became cloudy and then the solution was extracted with EA (20 ml×3). The organic layers were combined, directly powdered by rotary evaporation to dryness, and separated by column chromatography on silica gel (PE:EA=8:1), to obtain a pale purple solid (373.0 mg). Yield: 59.8%, m.p. 233-235° C.

$^1$H-NMR (300 MHz, $CDCl_3$) δ 3.61 (s, 3H, —COOC$\underline{H}_3$), 3.76 (s, 3H, —OC$\underline{H}_3$), 3.95 (s, 3H, —OC$\underline{H}_3$), 5.80 (s, 1H, —OCH—), 6.59-6.62 (m, 1H, Ar—$\underline{H}$), 6.74-6.79 (m, 2H, Ar—$\underline{H}$), 7.02 (s, 1H, Ar—H), 7.14-7.17 (m, 1H, Ar—$\underline{H}$), 7.32-7.34 (m, 1H, Ar—$\underline{H}$), 7.42-7.56 (m, 4H, Ar—$\underline{H}$), 7.65-7.67 (m, 2H, Ar—$\underline{H}$), 7.76-7.78 (m, 1H, Ar—$\underline{H}$), 8.41-8.44 (m, 1H, Ar—$\underline{H}$); EI-MS m/z: 530 [M+Na]$^+$.

(2) Methyl 2-(4-(3,4-dimethoxy-N-(methoxycarbonylmethyl)benzenesulfonamido) naphthalen-1-oxy)-benzeneacetate (5-2)

Compound (5-1) (373.0 mg, 734.9 mmol) was dissolved in DMF (5 ml), and potassium carbonate (203.1 mg, 1.5 mmol) and then methyl bromoacetate (102.2 μL, 1.1 mmol) were added and stirred at room temperature. After the reaction was complete by TLC (about 2 hrs), water was added to the solution, until the solution became cloudy. The solution was adjusted to pH 7 with a saturated $NH_4Cl$ solution, and then extracted with EA (3×). The organic layers were combined, washed with a saturated sodium chloride solution (3×), powdered by rotary evaporation to dryness, and then separated and purified by column chromatography (PE:EA=4:1), to obtain a pale red product (239 mg). Yield: 28.3%, m.p. 141-143° C.

$^1$H-NMR (300 MHz, CDCl$_3$) δ 3.53-3.78 (m, 9H, —OCH$_3$), 3.95 (s, 3H, —OCH$_3$), 4.21-4.27 (m, 1H, —NCH$_2$—), 4.68-4.76 (m, 1H, —NCH$_2$—), 5.79 (s, 1H, —OCH—), 6.55-6.57 (m, 1H, Ar—H), 6.87-6.89 (m, 1H, Ar—H), 7.07-7.09 (m, 1H, Ar—H), 7.17-7.19 (m, 1H, Ar—H), 7.43-7.66 (m, 8H, Ar—H), 7.94-8.02 (m, 1H, Ar—H), 8.45-8.47 (m, 1H, Ar—H); EI-MS m/z: 602 [M+Na]$^+$.

(3) 2-(4-(N-(carboxymethyl)-3,4-dimethoxybenzenesulfonamido))naphthalen-1-oxy) benzeneacetic acid (I-5)

Compound (5-2) (239.0 mg, 412.3 μmol) was dissolved in methanol (5 ml), and water (5 ml) and then LiOH (500.0 mg, 20.8 mmol) were added and stirred overnight at room temperature. After the reaction was complete by TLC (about 10 hrs), a small amount of water was added to the system until the solution became cloudy. The solution was adjusted to pH 4 with a hydrochloric acid solution. The solution became cloudy, and a purple solid was precipitated out, which was suctioned and dried, to obtain a pale purple solid (148.0 mg). Yield: 65.1%, m.p. 236-238° C.

$^1$H-NMR (300 MHz, CDCl$_3$) δ 3.77 (s, 3H, —OCH$_3$), 3.92 (s, 3H, —OCH$_3$), 4.02-4.16 (m, 1H, —NCH$_2$—), 5.05-5.11 (m, 1H, —NCH$_2$—), 5.74 (s, 1H, —OCH—), 6.71-6.73 (m, 1H, Ar—H), 6.82-6.85 (m, 1H, Ar—H), 6.99-7.19 (m, 2H, Ar—H), 7.30-7.49 (m, 6H, Ar—H), 7.64-7.95 (m, 3H, Ar—H), 8.33-8.40 (m, 1H, Ar—H); EI-MS HRMS (ESI): calcd. for C$_{28}$H$_{26}$NO$_9$S. [M+H]$^+$ 552.1323, found 552.1331.

Example 6

The synthesis method of Compound (1-2) was exactly the same as that in Example 1.

(1) Methyl 2-((4-(2,4,6-trimethoxybenzenesulfonamido)naphthalen-1-oxy)-benzene acetate (6-1)

Compound (1-2) (1.38 g, 4.5 mmol) was dissolved in CH$_2$Cl$_2$ (10.0 ml), and CF$_3$COOH (10.0 ml, 135.1 mmol) was added and stirred at room temperature. After the reaction was complete by TLC (about 0.5 hrs), the reaction solution was adjusted to pH 7 with a saturated Na$_2$CO$_3$ solution and extracted with EA (20 ml×3). The organic layers were combined, washed with a saturated sodium chloride solution (3×), dried over anhydrous sodium sulfate, and rotary evaporated to dryness, to obtain a grey solid 5, which was directly dissolved in THF without further treatment. 2,4,6-trimethoxyphenylsulfonyl chloride (1.4 g, 5.4 mmol) and then pyridine (542.6 μL, 6.7 mmol) was added and stirred at room temperature. After the reaction was complete by TLC (about 8 hrs), THF was rotary evaporated to dryness, and a small amount of acetone was added to dissolve the oil. A dilute hydrochloric acid solution was added until the solution became cloudy and then the solution was extracted with EA (20 ml×3). The organic layers were combined, directly powdered by rotary evaporation to dryness, and separated by column chromatography on silica gel (PE:EA=8:1), to obtain a pale purple solid (856.0 mg). Yield: 35.5%, m.p. 220-222° C. $^1$H-NMR (300 MHz, CDCl$_3$) δ 3.70 (s, 3H, —COOCH$_3$), 3.85-3.86 (m, 9H, —OCH$_3$), 5.81 (s, 1H, —OCH—), 6.78 (s, 2H, Ar—H), 6.88-6.91 (m, 1H, Ar—H), 7.38-7.41 (m, 5H, Ar—H), 7.56-7.58 (m, 2H, Ar—H), 8.04-8.06 (m, 1H, Ar—H), 8.27-8.30 (m, 1H, Ar—H); EI-MS m/z: 560 [M+Na]$^+$.

(2) Methyl 2-(4-(2,4,6-trimethoxy-N-(methoxycarbonylmethyl)benzenesulfonamido) naphthalen-1-oxy)-benzeneacetate (6-2)

Compound (7-1) (856.0 mg, 1.6 mmol) was dissolved in DMF (5 ml), and potassium carbonate (330.1 mg, 2.4 mmol) and then methyl bromoacetate (177.2 μL, 1.1 mmol) were added and stirred at room temperature. After the reaction was complete by TLC (about 2 hrs), water was added to the solution, until the solution became cloudy. The solution was adjusted to pH 7 with a saturated NH$_4$Cl solution, and then extracted with EA (3×). The organic layers were combined, washed with a saturated sodium chloride solution (3×), powdered by rotary evaporation to dryness, and then separated and purified by column chromatography (PE:EA=4:1), to obtain a pale red product (461.0 mg). Yield: 47.5%, m.p. 231-233° C. $^1$H-NMR (300 MHz, CDCl$_3$) δ 3.68-3.71 (m, 6H, —OCH$_3$), 3.84-3.86 (m, 9H, —OCH$_3$), 4.23-4.25 (m, 1H, —NCH$_2$—), 4.80-4.82 (m, 1H, —NCH$_2$—), 5.81 (s, 1H, —OCH—), 6.79 (s, 2H, Ar—H), 6.48-6.50 (m, 1H, Ar—H), 6.91-6.93 (m, 1H, Ar—H), 7.34-7.38 (m, 5H, Ar—H), 7.58-7.61 (m, 1H, Ar—H), 7.98-8.02 (m, 1H, Ar—H), 8.28-8.31 (m, 1H, Ar—H); EI-MS m/z: 632 [M+Na]$^+$.

(3) 2-(4-(N-(carboxymethyl)-2,4,6-trimethoxybenzenesulfonamido))naphthalen-1-oxy)benzeneacetic acid (I-6)

Compound (7-2) (461.0 mg, 756.2 μmol) was dissolved in methanol (5 ml), and water (5 ml) and then LiOH (500.0 mg, 20.8 mmol) were added and stirred overnight at room temperature. After the reaction was complete by TLC (about 10 hrs), a small amount of water was added to the system until the solution became cloudy. The solution was adjusted to pH 4 with a hydrochloric acid solution. The solution became cloudy, and a purple solid was precipitated out, which was suctioned and dried to obtain a pale purple solid (135.0 mg). Yield: 30.7%, m.p.>250° C. $^1$H-NMR (300 MHz, DMSO) δ 3.83-3.85 (m, 9H, —OCH$_3$), 4.80 (s, 2H, —NCH$_2$—), 5.87 (s, 1H, —OCH—), 6.46-6.48 (m, 1H, Ar—H), 6.80 (s, 2H, Ar—H), 6.91-7.93 (m, 1H, Ar—H), 7.35-7.40 (m, 5H, Ar—H), 7.57-7.59 (m, 1H, Ar—H), 7.99-8.03 (m, 1H, Ar—H), 8.30-8.33 (m, 1H, Ar—H); EI-MS HRMS (ESI): calcd. for C$_{29}$H$_{28}$NO$_{10}$S. [M+H]$^+$ 582.1413, found 582.1411.

Example 7

The synthesis method of Compound (1-2) was exactly the same as that in Example 1.

(1) Methyl 2-((4-(4-acetamidobenzenesulfonamido) naphthalen-1-oxy)-benzene acetate (7-1)

Compound (1-2) (720.0 mg, 1.8 mmol) was dissolved in CH$_2$Cl$_2$ (5.0 ml), and CF$_3$COOH (5.0 ml, 67.3 mmol) was added and stirred at room temperature. After the reaction was complete by TLC (about 1 hrs), the reaction solution was adjusted to pH 7 with a saturated Na$_2$CO$_3$ solution and extracted with EA (20 ml×3). The organic layers were combined, washed with a saturated sodium chloride solution (3×), dried over anhydrous sodium sulfate, and rotary evaporated to dryness, to obtain a grey solid which was directly dissolved in THF without further treatment. p-Acetamidophenylsulfonyl chloride (620.0 mg, 2.6 mmol) and then pyridine (285.0 μL, 3.5 mmol) were added and stirred at room temperature. After the reaction was complete by TLC (about 5 hrs), THF was rotary evaporated to dryness, and a small amount of acetone was added to dissolve the oil. A dilute hydrochloric acid solution was added until the solution became cloudy and then the solution was extracted with EA (20 ml×3). The organic layers were combined, directly powdered by rotary evaporation to dryness, and separated by column chromatography on silica gel (PE:EA=8:1), to obtain a purple solid (425.0 mg). Yield: 47.8%, m.p. 236.7-240.1° C. $^1$H-NMR (300 MHz, DMSO) δ 2.05 (s, 3H, —COC$H_3$), 3.64 (s, 3H, —COOC$H_3$), 6.20 (s, 1H, —OCH—), 6.80-6.83 (m, 1H, Ar—H), 6.91-6.94 (m, 1H, Ar—H), 7.41-7.56 (m, 7H, Ar—H), 7.64-7.67 (m, 4H, Ar—H), 7.93-7.96 (m, 1H, Ar—H), 8.22-8.25 (m, 1H, Ar—H), 9.89 (s, 1H, —NHS$O_2$—), 10.30 (s, 1H, —NHCO—); EI-MS m/z: 527 [M+Na]$^+$.

(2) Methyl 2-(4-(4-acetamido-N-(methoxycarbonylmethyl)benzenesulfonamido) naphthalen-1-oxy)-benzeneacetate (7-2)

Compound (8-1) (425.0 mg, 842.3 μmol) was dissolved in DMF (5 ml), and potassium carbonate (174.6 mg, 1.3 mmol) and then methyl bromoacetate (94.0 μL, 1.0 mmol) were added and stirred at room temperature. After the reaction was complete by TLC (about 4 hrs), water was added to the solution, until the solution became cloudy. The solution was adjusted to pH 7 with a saturated N$H_4$Cl solution. A pale red solid was precipitated out, which was suctioned and dried. 370.0 mg of the pale red solid was obtained. Yield: 76.1%, m.p. 178-180° C. $^1$H-NMR (300 MHz, DMSO) δ 2.10 (s, 3H, —COC$H_3$), 3.54-3.71 (m, 6H, —COOC$H_3$), 4.45-4.55 (m, 2H, —NC$H_2$—), 6.27 (s, 1H, —OCH—), 6.83-6.86 (m, 1H, Ar—H), 7.03-7.07 (m, 1H, Ar—H), 7.42-7.52 (m, 3H, Ar—H), 7.55-7.76 (m, 8H, Ar—H), 8.03-8.06 (m, 1H, Ar—H), 8.25-8.28 (m, 1H, Ar—H), 10.39-10.40 (m, 1H, —NHCO—); EI-MS m/z: 599 [M+Na]$^+$.

(3) 2-(4-(N-(carboxymethyl)-4-acetamidobenzenesulfonamido))naphthalen-1-oxy) benzeneacetic acid (I-7)

Compound (8-2) (370.0 mg, 642.0 μmol) was dissolved in methanol (15 ml), and water (5 ml) and then LiOH (800 mg, 33.0 mmol) were added and stirred at room temperature. After the reaction was complete by TLC (about 10 hrs), a small amount of water was added to the system until the solution became cloudy. The solution was adjusted to pH 3 with a hydrochloric acid solution. The solution became cloudy, and a yellow-white solid was precipitated out, which was suctioned and dried to obtain a solid (260.0 mg). Yield: 73.9%, m.p. 255.7-257° C. $^1$H-NMR (300 MHz, DMSO) δ 2.10 (s, 3H, —COC$H_3$), 4.25-4.49 (m, 2H, —NC$H_2$—), 6.08-6.09 (m, 1H, —OCH—), 6.82-6.85 (m, 1H, Ar—H), 7.09-7.11 (m, 1H, Ar—H), 7.42-7.76 (m, 11H, Ar—H), 8.02-8.05 (m, 1H, Ar—H), 8.28-8.31 (m, 1H, Ar—H), 10.37 (s, 1H, —NHCO—), 12.83-13.31 (m, 2H, —COOH); HRMS (ESI): calcd. for $C_{28}H_{24}N_2NaO_8S$. [M+Na]$^+$ 571.1146, found 571.117.

Example 8

The synthesis method of Compound (1-2) was exactly the same as that in Example 1.

(1) Methyl 2-((4-(4-nitrobenzenesulfonamido)naphthalen-1-oxy)-benzeneacetate (8-1)

Compound (1-2) (457 mg, 1.12 mmol) was dissolved in C$H_2$C$l_2$ (5 ml), and C$F_3$COOH (5 ml, 67 mmol) was added and stirred at room temperature. After the reaction was complete by TLC (30 min), the reaction solution was adjusted to pH 7 with a saturated N$a_2$C$O_3$ solution and extracted with EA (10 ml×3). The organic layers were combined, washed with a saturated sodium chloride solution (3×), dried over anhydrous sodium sulfate, and rotary evaporated to dryness, to obtain a grey-black solid which was dissolved in THF without further treatment. 4-nitrophenylsulfonyl chloride (298 mg, 1.35 mmol) and then pyridine (181 μL, 2.24 mmol) was added and stirred at room temperature. After the reaction was complete by TLC (about 12 hrs), THF was rotary evaporated to dryness, and a small amount of acetone was added to dissolve the oil. After direct powdering and separation by column chromatography on silica gel (PE:EA=8:1), a white solid (253 mg) was obtained. Yield: 45.8%, m.p. 218-221° C. $^1$H-NMR (300 MHz, DMSO) δ 3.66 (s, 3H, —COOC$H_3$), 6.22 (s, 1H, —OCH—), 6.83 (d, 1H, J=8.43, Ar—H), 6.97 (d, 1H, Ar—H, J=8.25, Ar—H), 7.43-7.54 (m, 5H, Ar—H), 7.63-7.65 (m, 2H, Ar—H), 7.85-7.90 (m, 3H, Ar—H), 8.24-8.35 (m, 3H, Ar—H), 10.41 (s, 1H, —NH—); EI-MS m/z: 515 [M+Na]$^+$.

(2) Methyl 2-(4-(4-nitro-N-(methoxycarbonylmethyl)benzenesulfonamido) naphthalene-1-oxy)-benzeneacetate (8-2)

Compound (9-1) (253 mg, 514 μmol) was dissolved in DMF (5 ml), and potassium carbonate (107 mg, 771 μmol) and then methyl bromoacetate (57 μL, 616 μmol) was added and stirred overnight at room temperature. After the reaction was complete by TLC, water was added to the solution, until the solution became cloudy. The solution was adjusted to pH 7 with a saturated N$H_4$Cl solution. A yellow solid was precipitated out, which was suctioned and dried to obtain a solid (199 mg). Yield: 68.6%, m.p. 235-237° C. $^1$H-NMR (300 MHz, DMSO) δ 3.56-3.72 (m, 6H, —COOC$H_3$), 4.50-4.56 (m, 1H, —NC$H_2$—), 4.70-4.73 (m, 1H, —NC$H_2$—), 6.27 (s, 1H, —OCH—), 6.84-6.87 (m, 1H, Ar—H), 7.13-7.16 (m, 2H, Ar—H), 7.42-7.50 (m, 3H, Ar—H), 7.57-7.69 (m, 4H, Ar—H), 7.89-7.96 (m, 3H, Ar—H), 8.30-8.33 (m, 3H, Ar—H); EI-MS m/z: 587 [M+Na]$^+$.

(3) 2-(4-(N-(carboxymethyl)-4-nitrobenzenesulfonamido))naphthalen-1-oxy) benzeneacetate (I-8)

Compound (9-2) (199.0 mg, 352.0 μmol) was dissolved in methanol (5 ml), and water (5 ml) and then LiOH (1.0 g, 42.0 mmol) were added and stirred overnight at room temperature. After the reaction was complete by TLC (about 10 hrs), a small amount of water was added to the system until the solution became cloudy. The solution was adjusted to pH 3 with a hydrochloric acid solution. The solution became cloudy, and a grey solid was precipitated out, which was suctioned and dried. 106.0 mg of the grey solid was obtained. Yield: 56.0%, m.p. 245-247° C. $^1$H-NMR (300 MHz, DMSO) δ 4.26-4.37 (m, 1H, —NC$H_2$—), 4.59-4.65 (m, 1H, —NC$H_2$—), 6.04 (s, 1H, —OCH—), 6.82-6.85 (m, 1H, Ar—H), 7.18-7.20 (m, 1H, Ar—H), 7.40-7.47 (m, 3H, Ar—H), 7.56-7.57 (m, 2H, Ar—H), 7.637.90 (m, 2H, Ar—H), 7.92-7.97 (m, 3H, Ar—H), 8.35-8.37 (m, 3H, Ar—H); HRMS (ESI): calcd. for $C_{26}H_{24}N_3O_9S$. [M+N$H_4$]$^+$ 554.1228, found 554.1239.

Example 9

The synthesis method of Compound (1-2) was exactly the same as that in Example 1.

(1) Methyl 2-((4-(4-fluorobenzenesulfonamido) naphthalen-1-oxy)-benzeneacetate (9-1)

Compound (1-2) (400 mg, 982 μmol) was dissolved in $CH_2Cl_2$ (5 ml), and $CF_3COOH$ (5 ml, 67 mmol) was added and stirred at room temperature. After the reaction was complete by TLC (30 min), the reaction solution was adjusted to pH 7 with a saturated $Na_2CO_3$ solution and, and extracted with EA (10 ml×3). The organic layers were combined, washed with a saturated sodium chloride solution (3×), dried over anhydrous sodium sulfate, and rotary evaporated to obtain a grey-black solid 5, which was dissolved in THF without further treatment. 4-fluorophenylsulfonyl chloride (228 mg, 1.10 mmol) and then pyridine (160 μL, 982 μmol) were added and stirred at room temperature. After the reaction was complete by TLC (about 12 hrs), THF was rotary evaporated to dryness, and a small amount of acetone was added to dissolve the oil. After direct powdering and separation by column chromatography on silica gel (PE: EA=8:1), a white solid (258 mg) was obtained. Yield: 56.5%, m.p. 126.2-128.7° C. $^1$H-NMR (300 MHz, DMSO) δ 3.66 (m, 3H, —COO$\underline{CH_3}$), 6.22 (s, 1H, —OCH—), 6.84 (d, 1H, J=8.43, Ar—$\underline{H}$), 6.97 (d, 1H, Ar—$\underline{H}$, J=8.31, Ar—$\underline{H}$), 7.30-7.36 (m, 2H, Ar—$\underline{H}$), 7.44-7.53 (m, 5H, Ar—$\underline{H}$), 7.63-7.69 (m, 4H, Ar—$\underline{H}$), 7.87 (d, 1H, J=8.01, Ar—$\underline{H}$), 8.25 (d, 1H, J=7.44, Ar—$\underline{H}$), 10.07 (s, 1H, J=7.44, Ar—$\underline{H}$); EI-MS m/z: 488 [M+Na]$^+$.

(2) Methyl 2-(4-(4-fluoro-N-(methoxycarbonylmethyl)benzenesulfonamido) naphthalen-1-oxy)-benzeneacetate (9-2)

Compound (10-1) (258 mg, 554 μmol) was dissolved in DMF (5 ml), and potassium carbonate (115 mg, 831 μmol) and then methyl bromoacetate (62 μL, 665 mol) were added and stirred overnight at room temperature. After the reaction was complete by TLC, water was added to the solution until the solution became cloudy. The solution was adjusted to pH 7 with a saturated $NH_4Cl$ solution. A pink solid was precipitated out, which was suctioned and dried, to obtain a solid (246 mg). Yield: 82.6%, m.p. 89-91° C. $^1$H-NMR (300 MHz, DMSO) δ 3.55-3.71 (m, 6H, —COO$\underline{CH_3}$), 4.40-4.51 (m, 1H, —N$\underline{CH_2}$—), 4.62-4.71 (m, 1H, —N$\underline{CH_2}$—), 6.27 (s, 1H, —OCH—), 6.84-6.88 (m, 1H, Ar—$\underline{H}$), 7.11-7.14 (m, 1H, Ar—$\underline{H}$), 7.35-7.70 (m, 11H, Ar—$\underline{H}$), 7.93-7.98 (m, 1H, Ar—$\underline{H}$), 8.28-8.33 (m, 1H, Ar—$\underline{H}$); EI-MS m/z: 560 [M+Na]$^+$.

(3) 2-(4-(N-(carboxymethyl)-4-fluorobenzenesulfonamido))naphthalen-1-oxy) benzeneacetic acid (I-9)

Compound (10-2) (246.0 mg, 458.0 μmol) was dissolved in methanol (5 ml), and water (5 ml) and then LiOH (1 g, 42 mmol) were added and stirred overnight at room temperature. After the reaction was complete by TLC (about 10 hrs), a small amount of water was added to the system until the solution became cloudy. The solution was adjusted to pH 6 with a hydrochloric acid solution. The solution became cloudy, and a white solid was precipitated out, which was suctioned and dried to obtain a white solid (190.0 mg). Yield: 81.5%, m.p. 133-134° C. $^1$H-NMR (300 MHz, DMSO) δ 4.25-4.35 (m, 1H, —N$\underline{CH_2}$—), 4.50-4.58 (m, 1H, —N$\underline{CH_2}$—), 6.07 (s, 1H, —OCH—), 6.83-6.86 (m, 1H, Ar—$\underline{H}$), 7.15-7.18 (m, 1H, Ar—$\underline{H}$), 7.37-7.73 (m, 11H, Ar—$\underline{H}$), 7.92-7.95 (m, 1H, Ar—$\underline{H}$), 8.27-8.30 (m, 1H, Ar—$\underline{H}$); EI-MS m/z: HRMS (ESI): calcd. for $C_{26}H_{24}FN_2O_7S$. [M+NH$_4$]$^+$ 522.1283, found 527.1295.

Example 10

The synthesis method of Compound (1-2) was exactly the same as that in Example 1.

(1) Methyl 2-((4-(4-trifluoromethylbenzenesulfonamido)naphthalen-1-oxy)-benzene acetate (10-1)

Compound (1-2) (800.0 mg, 2.0 mmol) was dissolved in $CH_2Cl_2$ (5.0 ml), and $CF_3COOH$ (5.0 ml, 67.3 mmol) was added and stirred at room temperature. After the reaction was complete by TLC (about 1 hrs), the reaction solution was adjusted to pH 7 with a saturated $Na_2CO_3$ solution and extracted with EA (20 ml×3). The organic layers were combined, washed with a saturated sodium chloride solution (3×), dried over anhydrous sodium sulfate, and rotary evaporated to dryness, to obtain a grey solid which was directly dissolved in THF without further treatment. 4-trifluoromethylphenylsulfonyl chloride (580.0 mg, 2.4 mmol) and then pyridine (318.0 μL, 4.0 mmol) were added and stirred at room temperature. After the reaction was complete by TLC (about 12 hrs), THF was rotary evaporated to dryness, and a small amount of acetone was added to dissolve the oil. A dilute hydrochloric acid solution was added until the solution became cloudy and then the solution was extracted with EA (20 ml×3). The organic layers were combined, directly powdered by rotary evaporation to dryness, and separated by column chromatography on silica gel (PE:EA=8:1), to obtain a pale red solid (417.0 mg). Yield: 40.1%, m.p. 144.5-146.8° C. $^1$H-NMR (300 MHz, CDCl$_3$) δ 3.77 (s, 3H, —COO$\underline{CH_3}$), 5.79 (s, 1H, —OCH—), 6.58-6.60 (m, 1H, Ar—$\underline{H}$), 6.79-6.80 (m, 1H, Ar—$\underline{H}$), 7.12-7.15 (m, 1H, Ar—$\underline{H}$), 7.37-7.50 (m, 5H, Ar—$\underline{H}$), 7.58-7.67 (m, 5H, Ar—$\underline{H}$), 7.76-7.79 (m, 2H, Ar—$\underline{H}$), 8.40-8.43 (m, 1H, Ar—$\underline{H}$); EI-MS m/z: 538 [M+Na]$^+$.

(2) Methyl 2-(4-(4-trifluoromethyl-N-(methoxycarbonylmethyl)benzenesulfonamido) naphthalen-1-oxy)-benzeneacetate (10-2)

Compound (13-1) (329.0 mg, 638.2 μmol) was dissolved in DMF (5 ml), and potassium carbonate (132.3 mg, 957.3 μmol) and then methyl bromoacetate (71.0 μL, 765.9 μmol) were added and stirred at room temperature. After the reaction was complete by TLC (about 2 hrs), water was added to the solution until the solution became cloudy. The solution was adjusted to pH 7 with a saturated NH$_4$Cl solution, and a white solid was precipitated out, which was suctioned and dried to obtain a solid (316.0 mg). Yield: 84.3%, m.p. 221.5-224.4° C. $^1$H-NMR (300 MHz, CDCl$_3$) δ 3.67-3.81 (m, 6H, —COO$\underline{CH_3}$), 4.14-4.23 (m, 1H, —N$\underline{CH_2}$—), 4.84-4.95 (m, 1H, —N$\underline{CH_2}$—), 5.81 (s, 1H, —OCH—), 6.55-6.58 (m, 1H, Ar—$\underline{H}$), 7.19-7.23 (m, 1H, Ar—$\underline{H}$), 7.42-7.71 (m, 5H, Ar—$\underline{H}$), 7.76-7.79 (m, 5H, Ar—$\underline{H}$), 7.83-7.88 (m, 2H, Ar—$\underline{H}$), 8.45-8.51 (m, 1H, Ar—H); EI-MS m/z: 610 [M+Na]$^+$.

(3) 2-(4-(N-(carboxymethyl)-4-trifluoromethylbenzenesulfonamido))naphthalen-1-oxy)benzeneacetic acid (I-10)

Compound (13-2) (316.0 mg, 538.0 μmol) was dissolved in methanol (15 ml), and water (5 ml) and then LiOH (800.0 mg, 33.0 mmol) were added and stirred at room temperature. After the reaction was complete by TLC (about 10 hrs), a small amount of water was added to the system until the solid was completely dissolved. The solution was adjusted to pH 2 with a hydrochloric acid solution. The solution became cloudy, and a white solid was precipitated out, which was stood, filtered, and dried. 254.0 mg of the white solid was obtained. Yield: 84.4%, m.p. 205-207° C. $^1$H-NMR (300 MHz, DMSO) δ 4.24-4.36 (m, 1H, —NC$\underline{H}_2$—), 4.58-4.65 (m, 1H, —NC$\underline{H}_2$—), 6.08 (s, 1H, —OC$\underline{H}$—), 6.85-6.87 (m, 1H, Ar—$\underline{H}$), 7.20-7.23 (m, 1H, Ar—$\underline{H}$), 7.36-7.50 (m, 5H, Ar—$\underline{H}$), 7.53-7.69 (m, 2H, Ar—$\underline{H}$), 7.83-7.95 (m, 5H, Ar—$\underline{H}$), 8.28-8.32 (m, 1H, Ar—$\underline{H}$) 13.12 (br, 2H, —COOH); EI-MS HRMS (ESI): calcd. for $C_{27}H_{20}F_3NO_7S$. $[M+Na]^+$ 582.0805, found 581.0809.

Example 11

The synthesis steps of Compound (3-1) were exactly the same as those in Example 3.

(1) 2-(4-(2,4,6-trimethylbenzenesulfonamido)naph-thalen-1-oxy)benzeneacetic acid (I-11)

Compound (3-1) (236.0 mg, 482 μmol) was dissolved in methanol (10 ml), and water (5 ml) and then LiOH (800.0 mg, 33.4 mmol) were added and stirred at room temperature. After the reaction was complete by TLC (about 10 hrs), a small amount of water was added to the system until the solid was completely dissolved. The solution was adjusted to pH 4 with a hydrochloric acid solution. The solution became cloudy, and a pale yellow solid was precipitated out, which was stood, suctioned, and dried. 222.0 mg of the pale yellow solid was obtained. Yield: 96.9%, m.p. 221-223° C. $^1$H-NMR (300 MHz, DMSO) δ 2.21 (s, 3H, —C$\underline{H}_3$), 2.29 (s, 6H, —C$\underline{H}_3$), 5.87 (s, 1H, —OC$\underline{H}$—), 6.76 (d, 1H, J=8.31, Ar—$\underline{H}$), 6.85 (d, 1H, J=8.31, Ar—$\underline{H}$), 6.91 (s, 2H, Ar—$\underline{H}$), 7.35-7.51 (m, 5H, Ar—$\underline{H}$), 7.58-7.64 (m, 2H, Ar—$\underline{H}$), 7.91-7.93 (m, 1H, Ar—$\underline{H}$), 8.25-8.28 (m, 1H, Ar—$\underline{H}$), 9.78 (s, 1H, —NH); EI-MS HRMS (ESI): calcd. for $C_{27}H_{29}N_2O_5S$. $[M+NH_4]^+$ 493.1792, found 493.1798.

Example 12

The synthesis steps of Compound (3-1) were exactly the same as those in Example 3.

(1) Methyl 2-(4-(2,4,6-trimethyl-N-(cyanomethyl)benzenesulfonamido)naphthalene-1-oxy)-benzeneac-etate (12-1)

Compound (3-1) (748.0 mg, 1.5 mmol) was dissolved in DMF (5 ml), and potassium carbonate (422.0 mg, 3.1 mmol) and then bromoacetonitrile (160.0 μL, 2.3 mmol) were added and stirred at room temperature. After the reaction was complete by TLC (about 2 hrs), water was added to the solution, until the solution became cloudy. The solution was adjusted to pH 7 with a saturated NH$_4$Cl solution, and a solid was precipitated out, which was stood, suctioned, and dried, to obtain a tan solid (640 mg). Yield: 79.2%, m.p. 245-247° C. $^1$H-NMR (300 MHz, CDCl$_3$) δ 2.26-2.35 (m, 9H, —C$\underline{H}_3$), 3.77-3.78 (m, 3H, —COOC$\underline{H}_3$), 4.44-4.50 (m, 1H, —NC$\underline{H}_2$—), 5.06-5.15 (m, 1H, —NC$\underline{H}_2$—), 5.85 (s, 1H, —OC$\underline{H}$—), 6.62-6.65 (m, 1H, Ar—$\underline{H}$), 6.82-6.85 (m, 2H, Ar—$\underline{H}$), 7.30-7.34 (m, 1H, Ar—$\underline{H}$), 7.45-7.50 (m, 5H, Ar—$\underline{H}$), 7.67-7.76 (m, 3H, Ar—$\underline{H}$), 8.46-8.49 (m, 1H, Ar—$\underline{H}$); EI-MS m/z: 551 [M+Na]$^+$.

(2) 2-(4-((N-(2H-tetrazol-5-yl)methyl)-2,4,6-trim-ethylbenzenesulfonamido) naphthalen-1-oxy)benze-neacetic acid (I-12)

Compound (15-1) (640.0 mg, 1.4 μmol) was dissolved in DMF (5 ml), and sodium azide (269 mg, 4.1 mmol) and then ammonium chloride (295 mg, 5.5 mmol) were added and heated to reflux. After the reaction was complete by TLC (about 5 hrs), water was added to the solution, and a solid was precipitated out, which was suctioned, dissolved in EA and washed with a 3 mol/L sodium hydroxide solution (3×). The aqueous layer was separated, washed with a small amount of EA (2×), and adjusted to pH 2 with hydrochloric acid. A solid was precipitated out, which was suctioned and dried to obtain a pale yellow solid (170 mg). Yield: 24.3%, m.p.>250° C. $^1$H-NMR (300 MHz, DMSO) δ 2.11-2.25 (m, 9H, —C$\underline{H}_3$), 5.24-5.33 (m, 2H, —NC$\underline{H}_2$—), 6.09-6.11 (m, 1H, —OC$\underline{H}$—), 6.84-6.91 (m, 3H, Ar—$\underline{H}$), 7.13-7.23 (m, 1H, Ar—$\underline{H}$), 7.35-7.45 (m, 5H, Ar—$\underline{H}$), 7.56-7.68 (m, 3H, Ar—$\underline{H}$), 8.21-8.26 (m, 1H, Ar—$\underline{H}$), 13.30 (br, 1H, —COOH); EI-MS HRMS (ESI): calcd. for $C_{29}H_{28}N_5O_5S$. $[M+H]^+$ 558.1817, found 558.1839.

Example 13

The synthesis steps of Compound (3-2) were as described in Example 3.

(1) 2-(4-(2,4,6-trimethyl-N-(2-(hydroxylamino)-2-oxoethylbenzenesulfonamido) naphthalen-1-oxy)-benzeneacetic acid (I-13)

Compound (3-2) (748.0 mg, 1.3 mmol) was dissolved in methanol (10 ml) and water (5 ml), and hydroxylamine hydrochloride (97.2 mg, 1.4 mmol) and sodium hydroxide (159.8 mg, 4.0 mmol) were added, and reacted for 5 hrs by heating to reflux under nitrogen atmosphere. Water was added and adjusted to pH 4-5. A white solid was precipitated out, which was suctioned and dried to obtain a product (426.0 mg). M.p. 233-236° C. $^1$H-NMR (300 MHz, DMSO) δ 2.34 (s, 3H, —C$\underline{H}_3$), 2.64 (s, 6H, —C$\underline{H}_3$), 4.80-4.97 (m, 2H, —NC$\underline{H}_2$—), 5.87 (s, 1H, —OC$\underline{H}$—), 6.46-6.48 (m, 1H, Ar—$\underline{H}$), 6.89-6.91 (m, 1H, Ar—$\underline{H}$), 7.19 (s, 2H, Ar—$\underline{H}$), 7.36-7.42 (m, 5H, Ar—$\underline{H}$), 7.56-7.58 (m, 2H, Ar—$\underline{H}$), 8.06-8.09 (m, 1H, Ar—$\underline{H}$), 8.25-8.28 (m, 1H, Ar—$\underline{H}$), 13.30 (br, 1H, —COOH); EI-MS HRMS (ESI): calcd. for $C_{29}H_{28}NO_7S$. $[M+H]^+$ 534.1507, found 534.1502.

Example 14

(1) Methyl 2-((4-tert-butoxycarbonylamino)naphtha-len-1-oxy)-(4-methoxyphenyl) acetate (14-1)

1-Hydroxy-4-nitronaphthalene (2.8 g, 14.8 mmol) was dissolved in methanol, and 5% palladium on carbon (78.0 mg, 0.8 mmol) was added. A hydrogen balloon was coupled, and the reaction was carried out at room temperature. After the reaction was complete by TLC, the palladium on carbon was filtered off. (Boc)$_2$O (6.5 g, 29.7 mmol) and triethyl-amine (4.1 ml, 29.7 mmol) were added to the filtrate, and stirred at room temperature under N$_2$ atmosphere. After the reaction was complete by TLC, methanol was rotary evaporated to dryness. The resultant material was dissolved in ethyl acetate, and washed with a dilute hydrochloric acid solution (pH 3-4) (3×). The organic layers were combined, and rotary evaporated to dryness, to obtain a grey-black solid (3.6 g) which was dissolved in DMF (10 ml) without further treatment. Methyl 4-methoxy-α-bromobenzeneacetate (3.8 g, 14.6 mmol) and potassium carbonate (2.9 g, 20.8 mmol) were added and reacted at room temperature. After the reaction was complete by TLC (about 2 hrs), water was added and then extracted with EA (3×). The organic layers were combined, washed with a saturated ammonium chloride solution (3×) and then a saturated sodium chloride solution (3×), powdered by rotary evaporation to dryness, and separated and purified by column chromatography on silica gel (PE:EA=8:1), to obtain a white solid (2.5 g). Yield: 40.9%, m.p. 203-205° C. $^1$H-NMR (300 MHz, CDCl$_3$) δ 1.55 (s, 9H, -Boc), 3.75 (s, 3H, —COOCH$_3$), 3.84 (s, 3H, —OCH$_3$), 5.77 (s, 1H, —OCH—), 6.75-6.78 (m, 1H, Ar—H), 6.71-6.74 (m, 1H, Ar—H), 6.95-6.97 (m, 2H, Ar—H), 7.56-7.58 (m, 4H, Ar—H), 7.85-7.87 (m, 1H, Ar—H), 8.46-8.48 (m, 1H, Ar—H); EI-MS m/z: 455 [M+NH$_4$]$^+$.

(2) Methyl 2-((4-(2,4,6-trimethylbenzenesulfonamido)naphthalen-1-oxy)-(4-methoxyphenyl)acetate (14-2)

Compound (17-1) (2.5 g, 5.7 mmol) was dissolved in CH$_2$Cl$_2$ (10.0 ml), and CF$_3$COOH (5.0 ml, 67.5 mmol) was added and stirred at room temperature. After the reaction was complete by TLC (about 1 hrs), the reaction solution was adjusted to pH 7 with a saturated Na$_2$CO$_3$ solution and extracted with EA (20 ml×3). The organic layers were combined, washed with a saturated sodium chloride solution (3×), dried over anhydrous sodium sulfate, and rotary evaporated to dryness, to obtain a grey solid which was directly dissolved in THF without further treatment. 2,4,6-trimethylphenylsulfonyl chloride (1.5 g, 6.8 mmol) and then pyridine (685.0 μL, 8.5 mmol) were added and stirred at room temperature. After the reaction was complete by TLC (about 5 hrs), THF was rotary evaporated to dryness, and a small amount of methanol was added to dissolve the oil. A small amount of dilute hydrochloric acid solution was added. The flask wall was scraped intensely, and there was a solid adhered to the blade. Then, a large amount of dilute hydrochloric acid was added, and a solid was precipitated out, which was suctioned and then slurried in diethyl ether together with the solid adhered to the blade. A solid was precipitated out, which was suctioned to obtain a purple solid (488.0 mg). Yield: 16.5%, m.p. 217-220° C. $^1$H-NMR (300 MHz, CDCl$_3$) δ 2.29 (s, 3H, —CH$_3$), 2.44 (s, 6H, —CH$_3$), 3.73 (s, 3H, —COOCH$_3$), 3.83 (s, 3H, —OCH$_3$), 5.73 (s, 1H, —OCH—), 6.50-6.52 (m, 1H, Ar—H), 6.61 (s, 1H, —NH—), 6.83-6.85 (m, 1H, Ar—H), 6.89 (s, 2H, Ar—H), 6.94-6.97 (m, 2H, Ar—H), 7.49-7.61 (m, 4H, Ar—H), 7.96-7.99 (m, 1H, Ar—H), 8.39-8.42 (m, 1H, Ar—H); EI-MS m/z: 542 [M+Na]$^+$.

(3) Methyl 2-(4-(2,4,6-trimethyl-N-(methoxycarbonylmethyl)benzenesulfonamido) naphthalen-1-oxy)-(4-methoxyphenyl)acetate (14-3)

Compound (17-2) (185.0 mg, 346.4 μmol) was dissolved in DMF (5 ml), and potassium carbonate (72.0 mg, 519.6 μmol) and then methyl bromoacetate (39.0 μL, 415.7 mmol) were added and stirred at room temperature. After the reaction was complete by TLC (about 2 hrs), water was added to the solution, until the solution became cloudy. The solution was adjusted to pH 7 with a saturated NH$_4$Cl solution, and a solid was precipitated out, which was suctioned and dried to obtain a tan solid (177 mg). Yield: 86.3%, m.p. 231-232° C. $^1$H-NMR (300 MHz, DMSO) δ 2.10 (s, 3H, —CH$_3$), 2.16 (s, 3H, —CH$_3$), 2.18 (s, 3H, —CH$_3$), 3.55-3.58 (m, 3H, —COOCH$_3$), 3.65-3.68 (m, 3H, —COOCH$_3$), 3.71-3.77 (m, 3H, —OCH$_3$), 4.43-4.52 (m, 1H, —NCH$_2$—), 4.72-4.79 (m, 1H, —NCH$_2$—), 6.21-6.23 (m, 1H, —OCH—), 6.83-6.7.02 (m, 4H, Ar—H), 7.37-7.57 (m, 6H, Ar—H), 7.74-7.79 (m, 1H, Ar—H), 8.22-8.25 (m, 1H, Ar—H); EI-MS m/z: 592 [M+H]$^+$.

(4) 2-(4-(N-(carboxymethyl)-2,4,6-trimethylbenzenesulfonamido))naphthalen-1-oxy)-(4-methoxyphenyl)acetic acid (I-14)

Compound (17-3) (145.0 mg, 245 μmol) was dissolved in methanol (10 ml), and water (5 ml) and then LiOH (500.0 mg, 21.0 mmol) were added and stirred at room temperature. After the reaction was complete by TLC (about 10 hrs), a small amount of water was added to the system until the solid was completely dissolved. The solution was adjusted to pH 2 with a hydrochloric acid solution. The solution became cloudy, and a grey solid was precipitated out, which was stood, suctioned, and dried. 110.0 mg of the grey solid was obtained. Yield: 78.0%, m.p. 240-242° C. $^1$H-NMR (300 MHz, DMSO) δ 2.12-2.19 (m, 9H, —CH$_3$), 3.75-3.77 (m, 3H, —OCH$_3$) 4.26-4.36 (m, 1H, —NCH$_2$—), 4.64-4.71 (m, 1H, —NCH$_2$—), 6.02-6.05 (m, 1H, —OCH—), 6.83-6.94 (m, 3H, Ar—H), 6.97-7.02 (m, 2H, Ar—H), 7.37-7.58 (m, 5H, Ar—H), 7.71-7.78 (m, 1H, Ar—H), 8.23-8.24 (m, 1H, Ar—H), 12.86-13.20 (m, 2H, —COOH); EI-MS HRMS (ESI): calcd. for C$_{30}$H$_{29}$NNaO$_8$S. [M+Na]$^+$ 586.1506, found 586.1519.

Example 15

(1) Methyl 2-((4-tert-butoxycarbonylamino)naphthalen-1-oxy)-(4-ethoxyphenyl) acetate (15-1)

1-Hydroxy-4-nitronaphthalene (2.8 g, 14.8 mmol) was dissolved in methanol, and 5% palladium on carbon (78.0 mg, 0.8 mmol) was added. A hydrogen balloon was coupled, and the reaction was carried out at room temperature. After the reaction was complete by TLC, the palladium on carbon was filtered off. (Boc)$_2$O (6.5 g, 29.7 mmol) and triethylamine (4.1 ml, 29.7 mmol) were added to the filtrate, and stirred at room temperature under N$_2$ atmosphere. After the reaction was complete by TLC, methanol was rotary evaporated to dryness. The resultant material was dissolved in ethyl acetate, and washed with a dilute hydrochloric acid solution (pH 3-4) (3×). The organic layers were combined, and rotary evaporated to dryness, to obtain a grey-black solid, which was dissolved in DMF (10 ml) without further treatment. Methyl 4-ethoxy-α-bromobenzeneacetate (4.0 g, 14.8 mmol) and potassium carbonate (3.1 g, 22.2 mmol) were added and reacted at room temperature. After the reaction was complete by TLC (about 2 hrs), water was added and then extracted with EA (3×). The organic layers were combined, washed with a saturated ammonium chloride solution (3×) and then a saturated sodium chloride solution (3×), powdered by rotary evaporation to dryness, and separated and purified by column chromatography on silica gel (PE:EA=8:1), to obtain a white solid (3.23 g). Yield: 48.3%, m.p. 165-167° C., $^1$H-NMR (300 MHz, CDCl$_3$) δ 1.24-1.26 (m, 3H, —CH$_2$CH$_3$), 1.55 (s, 9H, -Boc), 3.73 (s, 3H, —OCH$_3$), 3.99-4.06 (m, 2H, —CH$_2$CH$_3$), 5.76 (s, 1H, —OCH—), 6.69-6.72 (m, 1H, Ar—H), 6.78 (br, 1H, —NH—), 6.85-6.95 (m, 2H, Ar—H), 7.50-7.59 (m, 5H, Ar—H), 7.83-7.86 (m, 1H, Ar—H), 8.45-8.48 (m, 1H, Ar—H); EI-MS m/z: 469 [M+NH$_4$]$^+$.

(2) Methyl 2-((4-(2,4,6-trimethylbenzenesulfonamido)naphthalen-1-oxy)-(4-ethoxyphenyl)acetate (15-2)

Compound (18-1) (3.2 g, 7.2 mmol) was dissolved in CH$_2$Cl$_2$ (10.0 ml), and CF$_3$COOH (5.0 ml, 67.5 mmol) was added and stirred at room temperature. After the reaction was complete by TLC (about 1 hrs), the reaction solution was adjusted to pH 7 with a saturated Na$_2$CO$_3$ solution and extracted with EA (20 ml×3). The organic layers were combined, washed with a saturated sodium chloride solution (3×), dried over anhydrous sodium sulfate, and rotary evaporated to dryness, to obtain a grey solid which was directly dissolved in THF without further treatment. 2,4,6-trimethylphenylsulfonyl chloride (2.4 g, 1.5 mmol) and then pyridine (1.2 ml, 14.3 mmol) were added and stirred at room temperature. After the reaction was complete by TLC (about 5 hrs), THF was rotary evaporated to dryness, and a small amount of methanol was added to dissolve the oil. A small amount of dilute hydrochloric acid solution was added. The flask wall was scraped intensely, and there was a solid adhered to the blade. Then, a large amount of dilute hydrochloric acid was added, and a solid was precipitated out, which was suctioned and then slurried in diethyl ether together with the solid adhered to the blade. A solid was precipitated out, which was suctioned to obtain a purple solid (1.3 g). Yield: 34.6%, m.p. 208-209° C. $^1$H-NMR (300 MHz, CDCl$_3$) δ 1.25-1.30 (m, 3H, —CH$_2$CH$_3$), 2.29 (s, 3H, —CH$_3$), 2.44 (s, 6H, —CH$_3$), 3.73-3.74 (m, 3H, —OCH$_3$), 4.02-4.09 (m, 2H, —CH$_2$CH$_3$), 5.72 (s, 1H, —OCH—), 6.50-6.56 (m, 2H, Ar—H), 6.84-6.95 (m, 5H, Ar—H), 7.47-7.55 (m, 3H, Ar—H), 7.95-7.97 (m, 1H, Ar—H), 8.39-8.41 (m, 1H, Ar—H); EI-MS m/z: 551 [M+NH$_4$]$^+$, 556 [M+Na]$^+$.

(3) Methyl 2-(4-(2,4,6-trimethyl-N-(methoxycarbonylmethyl)benzenesulfonamido) naphthalen-1-oxy)-(4-ethoxyphenyl)acetate (15-3)

Compound (18-2) (1.3 g, 2.4 mmol) was dissolved in DMF (5 ml), and potassium carbonate (505.0 mg, 3.65 mmol) and then methyl bromoacetate (447.2 μL, 2.9 mmol) was added and stirred at room temperature. After the reaction was complete by TLC (about 2 hrs), water was added to the solution until the solution became cloudy. The solution was adjusted to pH 7 with a saturated NH$_4$Cl solution, and a solid was precipitated out, which was suctioned and dried to obtain a tan solid (631 mg). Yield: 42.8%, m.p. 215-216° C. $^1$H-NMR (300 MHz, CDCl$_3$) δ 1.40-1.46 (m, 3H, —CH$_2$CH$_3$), 2.21-2.31 (m, 9H, —CH$_3$), 4.04-4.08 (m, 2H, —CH$_2$CH$_3$), 4.35-4.40 (m, 1H, —NCH$_2$—), 4.81-4.89 (m, 1H, —NCH$_2$—), 5.75-5.76 (m, 1H, —OCH—), 6.59-6.63 (m, 1H, Ar—H), 6.74-6.77 (m, 2H, Ar—H), 6.92-6.97 (m, 2H, Ar—H), 7.39-7.57 (m, 5H, Ar—H), 7.72-7.74 (m, 1H, Ar—H), 8.37-8.39 (m, 1H, Ar—H); EI-MS m/z: 606 [M+H]$^+$.

(4) 2-(4-(N-(carboxymethyl)-2,4,6-trimethylbenzenesulfonamido))naphthalen-1-oxy)-(4-ethoxyphenyl)acetic acid (I-15)

Compound (18-3) (631.0 mg, 1.0 mmol) was dissolved in methanol (10 ml), and water (5 ml) and then LiOH (500.0 mg, 20.88 mmol) were added and stirred at room temperature. After the reaction was complete by TLC (about 10 hrs), a small amount of water was added to the system until the solid was completely dissolved. The solution was adjusted to pH 2 with a hydrochloric acid solution. The solution became cloudy, and a grey solid was precipitated out, which was stood, suctioned, and dried. 254.0 mg of the grey solid was obtained. Yield: 41.2%, m.p. 215-218° C. $^1$H-NMR (300 MHz, CDCl$_3$) δ1.45 (t, 3H, J=6.93, —CH$_2$CH$_3$), 2.20-2.27 (m, 9H, —CH$_3$), 4.08 (q, 2H, J=6.93, —CH$_2$CH$_3$), 4.19-4.25 (m, 1H, —NCH$_2$—), 5.24-5.30 (m, 1H, —NCH$_2$—), 5.65 (s, 1H, —OCH—), 6.53-6.56 (m, 1H, Ar—H), 6.76 (s, 2H, Ar—H), 6.98-7.01 (m, 2H, Ar—H), 7.38-7.45 (m, 3H, Ar—H), 7.58-7.64 (m, 3H, Ar—H), 8.30-8.33 (m, 1H, Ar—H); EI-MS HRMS (ESI): calcd. for C$_{31}$H$_{31}$NNaO$_8$S. [M+Na]$^+$ 600.1663, found 600.1652.

Example 16

(1) Methyl 2-((4-tert-butoxycarbonylamino)naphthalen-1-oxy)-(4-acetamidophenyl) acetate (16-1)

1-Hydroxy-4-nitronaphthalene (2.8 g, 14.8 mmol) was dissolved in methanol, and 5% palladium on carbon (78.0 mg, 0.8 mmol) was added. A hydrogen balloon was coupled, and the reaction was carried out at room temperature. After the reaction was complete by TLC, the palladium on carbon was filtered off. (Boc)$_2$O (6.5 g, 29.7 mmol) and triethylamine (4.1 ml, 29.7 mmol) were added to the filtrate, and stirred at room temperature under N$_2$ atmosphere. After the reaction was complete by TLC, methanol was rotary evaporated to dryness. The resultant material was dissolved in ethyl acetate, and washed with a dilute hydrochloric acid solution (pH 3-4) (3×). The organic layers were combined, and rotary evaporated to dryness, to obtain a grey-black solid, which was dissolved in DMF (10 ml) without further treatment. Methyl 4-acetamido-α-bromobenzeneacetate (4.2 g, 14.8 mmol) and potassium carbonate (3.1 g, 22.2 mmol) were added and reacted at room temperature. After the reaction was complete by TLC (about 2 hrs), water was added and then extracted with EA (3×). The organic layers were combined, washed with a saturated ammonium chloride solution (3×) and then a saturated sodium chloride solution (3×), powdered by rotary evaporation to dryness, and separated and purified by column chromatography on silica gel (PE:EA=8:1), to obtain a white solid (1.7 g). Yield: 24.7%, m.p. 207-209° C. $^1$H-NMR (300 MHz, CDCl$_3$) δ 1.55 (s, 9H, -Boc), 2.05 (s, 3H, NHCOCH$_3$), 3.75 (s, 3H, —COOCH$_3$), 3.84 (s, 3H, —OCH$_3$), 5.79 (s, 1H, —OCH—), 6.77-6.79 (m, 1H, Ar—H), 6.73-6.76 (m, 1H, Ar—H), 6.97-6.99 (m, 2H, Ar—H), 7.57-7.60 (m, 4H, Ar—H), 7.87-7.89 (m, 1H, Ar—H), 8.46-8.48 (m, 1H, Ar—H), 9.89 (s, 1H, —NHSO$_2$—); EI-MS m/z: 482 [M+NH$_4$]$^+$.

(2) Methyl 2-((4-(2,4,6-trimethylbenzenesulfonamido)naphthalen-1-oxy)-(4-acetamidophenyl)acetate (16-2)

Compound (19-1) (1.7 g, 4.7 mmol) was dissolved in CH$_2$Cl$_2$ (10.0 ml), and CF$_3$COOH (5.0 ml, 67.5 mmol) was added and stirred at room temperature. After the reaction was complete by TLC (about 1 hrs), the reaction solution was adjusted to pH 7 with a saturated Na$_2$CO$_3$ solution and extracted with EA (20 ml×3). The organic layers were combined, washed with a saturated sodium chloride solution (3×), dried over anhydrous sodium sulfate, and rotary evaporated to dryness, to obtain a grey solid which was directly dissolved in THF without further treatment. 2,4,6-trimethylphenylsulfonyl chloride (1.5 g, 7.0 mmol) and then pyridine (751.7 µL, 9.3 mmol) were added and stirred at room temperature. After the reaction was complete by TLC (about 5 hrs), THF was rotary evaporated to dryness, and a small amount of methanol was added to dissolve the oil. A small amount of a dilute hydrochloric acid solution was added. The flask wall was scraped intensely, and there was a solid adhered to the blade. Then, a large amount of dilute hydrochloric acid was added, and a solid was precipitated out, which was suctioned and then slurried in diethyl ether together with the solid adhered to the blade. A solid was precipitated out, which was suctioned to obtain a purple solid (1.04 g). Yield: 40.8%, m.p. 221-223° C., $^1$H-NMR (300 MHz, DMSO) δ 2.29 (s, 3H, —CH$_3$), 2.44 (s, 6H, —CH$_3$), 2.06 (s, 3H, —NHCOCH$_3$), 3.73 (s, 3H, —COOCH$_3$), 5.82 (s, 1H, —OCH—), 6.51-6.53 (m, 1H, Ar—H), 6.85-6.87 (m, 1H, Ar—H), 6.90 (s, 2H, Ar—H), 6.96-6.98 (m, 2H, Ar—H), 7.51-7.63 (m, 4H, Ar—H), 7.98-8.01 (m, 1H, Ar—H), 8.41-8.43 (m, 1H, Ar—H), 10.28 (s, 1H, —NHCO—); EI-MS m/z: 569 [M+Na]$^+$.

(3) Methyl 2-(4-(2,4,6-trimethyl-N-(methoxycarbonylmethyl)benzenesulfonamido) naphthalen-1-oxy)-(4-acetamidophenyl)acetate (16-3)

Compound (19-2) (1.04 g, 1.9 mmol) was dissolved in DMF (5 ml), and potassium carbonate (525.9 mg, 3.8 mmol) and then methyl bromoacetate (444.6 µL, 2.9 mmol) were added and stirred at room temperature. After the reaction was complete by TLC (about 2 hrs), water was added to the solution, until the solution became cloudy. The solution was adjusted to pH 7 with a saturated NH$_4$Cl solution, and a solid was precipitated out, which was suctioned and dried to obtain a tan solid (740.0 mg). Yield: 62.9%, m.p. 235-237° C.

$^1$H-NMR (300 MHz, DMSO) δ 2.06 (s, 3H, —COCH$_3$), 2.11 (s, 3H, —CH$_3$), 2.17 (s, 3H, —CH$_3$), 2.19 (s, 3H, —CH$_3$), 3.55-3.58 (m, 3H, —COOCH$_3$), 3.65-3.68 (m, 3H, —COOCH$_3$), 4.45-4.54 (m, 1H, —NCH$_2$—), 4.74-4.81 (m, 1H, —NCH$_2$—), 6.23-6.25 (m, 1H, —OCH—), 6.85-6.7.04 (m, 4H, Ar—H), 7.39-7.60 (m, 5H, Ar—H), 7.73-7.76 (m, 1H, Ar—H), 7.96-7.98 (m, 1H, Ar—H), 8.24-8.27 (m, 1H, Ar—H), 10.26 (s, 1H, —NHCO—); EI-MS m/z: 519 [M+H]$^+$.

(4) 2-(4-(N-(carboxymethyl)-2,4,6-trimethylbenzenesulfonamido))naphthalen-1-oxy)-(4-acetamidophenyl)acetic acid (I-16)

Compound (19-3) (740.0 mg, 1.2 mmol) was dissolved in methanol (10 ml), and water (5 ml) and then LiOH (500.0 mg, 21.0 mmol) were added and stirred at room temperature. After the reaction was complete by TLC (about 10 hrs), a small amount of water was added to the system until the solid was completely dissolved. The solution was adjusted to pH 2 with a hydrochloric acid solution. The solution became cloudy, and a grey solid was precipitated out, which was stood, suctioned, and dried. 320.0 mg of the grey solid was obtained. Yield: 45.4%, m.p. 243-245° C. $^1$H-NMR (300 MHz, DMSO) δ 2.05 (s, 3H, —COCH$_3$), 2.11-2.18 (m, 9H, —CH$_3$), 4.24-4.34 (m, 1H, —NCH$_2$—), 4.62-4.69 (m, 1H, —NCH$_2$—), 6.00-6.03 (m, 1H, —OCH—), 6.81-6.92 (m, 3H, Ar—H), 6.95-7.00 (m, 2H, Ar—H), 7.35-7.56 (m, 5H, Ar—H), 7.69-7.76 (m, 1H, Ar—H), 8.21-8.23 (m, 1H, Ar—H), 10.30 (s, 1H, —NHCO—), 12.86-13.20 (m, 2H, —COOH); EI-MS HRMS (ESI): calcd. for C$_{31}$H$_{31}$N$_2$O$_8$S. [M+H]$^+$ 591.1706, found 591.1714.

Example 17

(1) Methyl 2-((4-tert-butoxycarbonylamino)naphthalen-1-oxy)-(4-isopropoxyphenyl) acetate (17-1)

1-Hydroxy-4-nitronaphthalene (2.8 g, 14.8 mmol) was dissolved in methanol, and 5% palladium on carbon (78.0 mg, 0.8 mmol) was added. A hydrogen balloon was coupled, and the reaction was carried out at room temperature. After the reaction was complete by TLC, the palladium on carbon was filtered off. (Boc)$_2$O (6.5 g, 29.7 mmol) and triethylamine (4.1 ml, 29.7 mmol) were added to the filtrate, and stirred at room temperature under N$_2$ atmosphere. After the reaction was complete by TLC, methanol was rotary evaporated to dryness. The resultant material was dissolved in ethyl acetate, and washed with a dilute hydrochloric acid solution (pH 3-4) (3×). The organic layers were combined, and rotary evaporated to dryness, to obtain a grey-black solid, which was dissolved in DMF (10 ml) without further treatment. Methyl 4-isopropoxy-α-bromobenzeneacetate (4.3 g, 14.8 mmol) and potassium carbonate (3.0 g, 22.2 mmol) were added and reacted at room temperature. After the reaction was complete by TLC (about 2 hrs), water was added and then extracted with EA (3×). The organic layers were combined, washed with a saturated ammonium chloride solution (3×) and then a saturated sodium chloride solution (3×), powdered by rotary evaporation to dryness, and separated and purified by column chromatography on silica gel (PE:EA=8:1), to obtain a white solid (1.5 g). Yield: 21.5%, m.p. 170-172° C.

$^1$H-NMR (300 MHz, CDCl$_3$) δ 1.45-1.47 (m, 6H, —CH(CH$_3$)$_2$), 1.62 (s, 9H, -Boc), 3.81 (s, 3H, —OCH$_3$), 4.62-4.66 (m, 1H, —CH(CH$_3$)$_2$), 5.78 (s, 1H, —OCH—), 6.74-6.81 (m, 2H, Ar—H), 6.98-7.01 (m, 1H, Ar—H), 7.53-7.67 (m, 4H, Ar—H), 7.89-7.98 (m, 2H, Ar—H), 8.50-8.53 (m, 1H, Ar—H); EI-MS m/z: 483 [M+NH$_4$]$^+$.

(2) Methyl 2-((4-(2,4,6-trimethoxybenzenesulfonamido)naphthalen-1-oxy)-(4-isopropoxyphenyl)acetate (17-2)

Compound (20-1) (1.5 g, 4.1 mmol) was dissolved in CH$_2$Cl$_2$ (10.0 ml), and CF$_3$COOH (5.0 ml, 67.5 mmol) was added and stirred at room temperature. After the reaction was complete by TLC (about 1 hrs), the reaction solution was adjusted to pH 7 with a saturated Na$_2$CO$_3$ solution and extracted with EA (20 ml×3). The organic layers were combined, washed with a saturated sodium chloride solution (3×), dried over anhydrous sodium sulfate, and rotary evaporated to dryness, to obtain a grey solid which was directly dissolved in THF without further treatment. 2,4,6-trimethylphenylsulfonyl chloride (1.1 g, 4.9 mmol) and then pyridine (496.0 µL, 6.2 mmol) were added and stirred at room temperature. After the reaction was complete by TLC (about 5 hrs), THF was rotary evaporated to dryness, and a small amount of methanol was added to dissolve the oil. A small amount of a dilute hydrochloric acid solution was added. The flask wall was scraped intensely, and there was a solid adhered to the blade. Then, a large amount of dilute hydrochloric acid was added, and a solid was precipitated out, which was suctioned and then slurried in diethyl ether together with the solid adhered to the blade. A solid was precipitated out, which was suctioned to obtain a purple solid (890.0 mg). Yield: 39.6%, m.p. 211-213° C. $^1$H-NMR (300 MHz, CDCl$_3$) δ 1.20-1.26 (m, 6H, —CH(CH$_3$)$_2$), 2.29 (s, 3H, —CH$_3$), 2.43 (s, 6H, —CH$_3$), 3.74 (m, 3H, —OCH$_3$), 4.57-4.61 (m, 1H, —CH(CH$_3$)$_2$), 5.67 (s, 1H, —OCH—), 6.48-6.55 (m, 2H, Ar—H), 6.83-6.94 (m, 4H, Ar—H), 7.48-7.54 (m, 3H, Ar—H), 7.80-7.81 (m, 1H, Ar—H), 7.96-7.99 (m, 1H, Ar—H), 8.38-8.41 (m, 1H, Ar—H); EI-MS m/z: 570 [M+Na]$^+$.

(3) Methyl 2-(4-(2,4,6-trimethoxy-N-(methoxycarbonylmethyl)benzenesulfonamido) naphthalen-1-oxy)-(4-isopropoxyphenyl)acetate (17-3)

Compound (20-2) (890.0 mg, 1.63 mmol) was dissolved in DMF (5 ml), and potassium carbonate (449.2 mg, 3.3 mmol) and then methyl bromoacetate (180.8 μL, 2.0 mmol) were added and stirred at room temperature. After the reaction was complete by TLC (about 2 hrs), water was added to the solution, until the solution became cloudy. The solution was adjusted to pH 7 with a saturated NH$_4$Cl solution, and a solid was precipitated out, which was suctioned and dried to obtain a tan solid (600.0 mg). Yield: 59.6%, m.p. 227-229° C. $^1$H-NMR (300 MHz, CDCl$_3$) δ 1.38-1.41 (m, 6H, —CH(CH$_3$)$_2$), 2.20-2.28 (m, 9H, —CH$_3$), 3.66-3.68 (m, 6H, —COOCH$_3$), 4.34-4.39 (m, 1H, —NCH$_2$—), 4.56-4.62 (m, 1H, —CH(CH$_3$)$_2$), 4.87-4.95 (m, 1H, —NCH$_2$—), 5.70-5.71 (m, 1H, —OCH—), 6.55-6.59 (m, 1H, Ar—H), 6.74-6.76 (m, 2H, Ar—H), 6.91-6.96 (m, 1H, Ar—H), 7.37-7.50 (m, 5H, Ar—H), 7.70-7.76 (m, 2H, Ar—H), 8.32-8.40 (m, 1H, Ar—H); EI-MS m/z: 642 [M+Na]$^+$.

(4) 2-(4-(N-(carboxymethyl)-2,4,6-trimethoxybenzenesulfonamido))naphthalen-1-oxy)-(4-isopropoxyphenyl)acetic acid (I-17)

Compound (20-3) (600.0 mg, 968.2 μmol) was dissolved in methanol (10 ml), and water (5 ml) and then LiOH (500.0 mg, 20.9 mmol) were added and stirred at room temperature. After the reaction was complete by TLC (about 10 hrs), a small amount of water was added to the system until the solid was completely dissolved. The solution was adjusted to pH 2 with a hydrochloric acid solution. The solution became cloudy, and a grey solid was precipitated out, which was stood, suctioned, and dried. 325.0 mg of the grey solid was obtained. Yield: 56.7%. $^1$H-NMR (300 MHz, CDCl$_3$) δ 1.33-1.35 (m, 6H, —CH(CH$_3$)$_2$), 2.12 (s, 3H, —CH$_3$), 2.20 (s, 6H, —CH$_3$), 4.10-4.16 (m, 1H, —NCH$_2$—), 4.53-4.59 (m, 1H, —CH(CH$_3$)$_2$), 5.15-5.21 (m, 1H, —NCH$_2$—), 5.55 (s, 1H, —OCH—), 6.45-6.47 (m, 1H, Ar—H), 6.69 (s, 2H, Ar—H), 6.90-6.93 (m, 1H, Ar—H), 7.32-7.37 (m, 3H, Ar—H), 7.51-7.53 (m, 3H, Ar—H), 7.82-7.84 (m, 1H, Ar—H), 8.22-8.25 (m, 1H, Ar—H); EI-MS HRMS (ESI): calcd. for C$_{32}$H$_{34}$NO$_8$S. [M+H]$^+$ 592.1923, found 592.1931.

Example 18

(1) Methyl 2-((4-tert-butoxycarbonylamino)naphthalen-1-oxy)-(4-fluorophenyl) acetate (18-1)

1-Hydroxy-4-nitronaphthalene (2.8 g, 14.8 mmol) was dissolved in methanol, and 5% palladium on carbon (78.0 mg, 0.8 mmol) was added. A hydrogen balloon was coupled, and the reaction was carried out at room temperature. After the reaction was complete by TLC, the palladium on carbon was filtered off. (Boc)$_2$O (6.5 g, 29.7 mmol), and triethylamine (4.1 ml, 29.7 mmol) were added to the filtrate, and stirred at room temperature under N$_2$ atmosphere. After the reaction was complete by TLC, methanol was rotary evaporated to dryness. The resultant material was dissolved in ethyl acetate, and washed with a dilute hydrochloric acid solution (pH 3-4) (3×). The organic layers were combined, and rotary evaporated to dryness, to obtain a grey-black solid, which was dissolved in DMF (10 ml) without further treatment. Methyl 4-fluoro-α-bromobenzeneacetate (4.39 g, 17.8 mmol) and potassium carbonate (3.07 g, 22.2 mmol) were added and reacted at room temperature. After the reaction was complete by TLC (about 2 hrs), water was added and then extracted with EA (3×). The organic layers were combined, washed with a saturated ammonium chloride solution (3×) and then a saturated sodium chloride solution (3×), powdered by rotary evaporation to dryness, and separated and purified by column chromatography on silica gel (PE:EA=8:1), to obtain an orange solid (1.3 g). Yield: 20.7%, m.p. 189-192° C. $^1$H-NMR (300 MHz, CDCl$_3$) δ 1.56 (s, 9H, -Boc), 3.75 (s, 3H, —COOCH$_3$), 5.79 (s, 1H, —OCH—), 6.67-6.69 (m, 2H, Ar—H), 7.04-7.06 (m, 2H, Ar—H), 7.39-7.55 (m, 4H, Ar—H), 7.82-7.85 (m, 1H, Ar—H), 8.43-8.45 (m, 1H, Ar—H); EI-MS m/z: 443 [M+NH$_4$]$^+$.

(2) Methyl 2-((4-(2,4,6-trimethoxybenzenesulfonamido)naphthalen-1-oxy)-(4-fluorophenyl)acetate (18-2)

Compound (21-1) (1.3 g, 5.7 mmol) was dissolved in CH$_2$Cl$_2$ (10.0 ml), and CF$_3$COOH (5.0 ml, 67.5 mmol) was added and stirred at room temperature. After the reaction was complete by TLC (about 1 hrs), the reaction solution was adjusted to pH 7 with a saturated Na$_2$CO$_3$ solution and extracted with EA (20 ml×3). The organic layers were combined, washed with a saturated sodium chloride solution (3×), dried over anhydrous sodium sulfate, and rotary evaporated to dryness, to obtain a grey solid which was directly dissolved in THF without further treatment. 2,4,6-trimethylphenylsulfonyl chloride (1.3 g, 6.1 mmol) and then pyridine (492.3 μL, 6.1 mmol) were added and stirred at room temperature. After the reaction was complete by TLC (about 5 hrs), THF was rotary evaporated to dryness, and a small amount of methanol was added to dissolve the oil. A small amount of a dilute hydrochloric acid solution was added. The flask wall was scraped intensely, and there was a solid adhered to the blade. Then, a large amount of dilute hydrochloric acid was added, and a solid was precipitated out, which was suctioned and then slurried in diethyl ether together with the solid adhered to the blade. A solid was precipitated out, which was suctioned to obtain a purple solid (723.0 mg). Yield: 46.6%, m.p. 209-211° C. $^1$H-NMR (300 MHz, CDCl$_3$) δ 2.18 (s, 3H, —CH$_3$), 2.27 (s, 3H, —CH$_3$), 2.35 (s, 3H, —CH$_3$), 3.73 (s, 3H, —COOCH$_3$), 5.76 (s, 1H, —OCH—), 6.49-6.55 (m, 2H, Ar—H), 6.89 (s, 2H, Ar—H), 7.09-7.16 (m, 2H, Ar—H), 7.51-7.65 (m, 4H, Ar—H), 7.95-8.00 (m, 1H, Ar—H), 8.38-8.43 (m, Ar—H); EI-MS m/z: 525 [M+NH$_4$]$^+$.

(3) Methyl 2-(4-(2,4,6-trimethoxy-N-(methoxycarbonylmethyl)benzenesulfonamido) naphthalen-1-oxy)-(4-fluorophenyl)acetate (18-3)

Compound (21-2) (185.0 mg, 346.4 μmol) was dissolved in DMF (5 ml), and potassium carbonate (295.3 mg, 2.1 mmol) and then methyl bromoacetate (158.5 μL, 1.7 mmol) were added and stirred at room temperature. After the reaction was complete by TLC (about 2 hrs), water was added to the solution, until the solution became cloudy. The solution was adjusted to pH 7 with a saturated NH₄Cl solution, and a solid was precipitated out, which was suctioned and dried to obtain a tan solid (478 mg). Yield: 57.9%, m.p. 232-235° C. $^1$H-NMR (300 MHz, CDCl$_3$) δ 2.21 (s, 3H, —CH$_3$), 2.26 (s, 3H, —CH$_3$), 2.30 (s, 3H, —CH$_3$), 3.67-3.69 (m, 3H, —COOCH$_3$), 3.75-3.77 (m, 3H, —COOCH$_3$), 4.35-4.41 (m, 3H, —NCH$_2$), 4.87-4.98 (m, 1H, —NCH$_2$—), 5.80-5.81 (m, 1H, —OCH—), 6.61-6.63 (m, 1H, Ar—H), 6.76-6.78 (m, 2H, Ar—H), 7.12-7.16 (m, 2H, Ar—H), 7.37-7.56 (m, 3H, Ar—H), 7.63-7.80 (m, 3H, Ar—H), 8.37-8.40 (m, 1H, Ar—H); EI-MS m/z: 580 [M+H]⁺.

(4) 2-(4-(N-(carboxymethyl)-2,4,6-trimethoxybenzenesulfonamido))naphthalen-1-oxy)-(4-fluorophenyl) acetic acid (I-18)

Compound (21-3) (478.0 mg, 824.7 μmol) was dissolved in methanol (10 ml), and water (5 ml) and then LiOH (500.0 mg, 21.0 mmol) were added and stirred at room temperature. After the reaction was complete by TLC (about 10 hrs), a small amount of water was added to the system until the solid was completely dissolved. The solution was adjusted to pH 2 with a hydrochloric acid solution. The solution became cloudy, and a grey solid was precipitated out, which was stood, suctioned, and dried. 212.0 mg of the grey solid was obtained. Yield: 44.4%. $^1$H-NMR (300 MHz, CDCl$_3$) δ 2.22 (s, 3H, —CH$_3$), 2.29 (s, 6H, —CH$_3$), 4.21-4.27 (m, 1H, —NCH$_2$—), 5.27-5.33 (m, 1H, —NCH$_2$—), 5.73 (s, 1H, —OCH—), 6.56-6.59 (m, 1H, Ar—H), 6.78 (s, 2H, Ar—H), 7.18-7.24 (m, 2H, Ar—H), 7.45-7.48 (m, 3H, Ar—H), 7.59-7.62 (m, 1H, Ar—H), 7.73-7.78 (m, 2H, Ar—H), 8.31-8.35 (m, 1H, Ar—H); EI-MS HRMS (ESI): calcd. for C$_{29}$H$_{26}$FNNaO$_7$S. [M+Na]⁺ 574.1306, found 574.1304.

Example 19

The synthesis of Compound (14-2) was the same as that in Example 14.

(1) Methyl 2-(4-(2,4,6-trimethyl-N-(cyanomethyl) benzenesulfonamido)naphthalene-1-oxy)-(4-methoxyphenyl)acetate (19-1)

Compound (14-2) (931.0 mg, 1.8 mmol) was dissolved in DMF (5 ml), and potassium carbonate (371.4 mg, 2.7 mmol) and then bromoacetonitrile (149.8 μL, 2.2 mmol) were added and stirred at room temperature. After the reaction was complete by TLC (about 2 hrs), water was added to the solution, until the solution became cloudy. The solution was adjusted to pH 7 with a saturated NH₄Cl solution, and a solid was precipitated out, which was stood, suctioned, and dried to obtain a tan solid (720.0 mg). Yield: 71.9%, m.p. 234-235° C. $^1$H-NMR (300 MHz, CDCl$_3$) δ 2.16-2.22 (m, 9H, —CH$_3$), 3.67-3.68 (m, 3H, —COOCH$_3$), 3.76-3.77 (m, 3H, —OCH$_3$), 4.34-4.41 (m, 1H, —NCH$_2$—), 4.97-5.06 (m, 1H, —NCH$_2$—), 5.70 (s, 1H, —OCH—), 6.52-6.55 (m, 1H, Ar—H), 6.73-6.75 (m, 2H, Ar—H), 6.86-6.91 (m, 2H, Ar—H), 7.21-7.25 (m, 2H, Ar—H), 7.37-7.64 (m, 4H, Ar—H), 8.34-8.37 (m, 1H, Ar—H); EI-MS m/z: 581 [M+Na]⁺.

(2) 2-(4-((N-(2H-tetrazol-5-yl)methyl)-2,4,6-trimethylbenzenesulfonamido) naphthalen-1-oxy)-(4-methoxyphenyl)acetic acid (I-19)

Compound (24-1) (720.0 mg, 1.4 μmol) was dissolved in DMF (5.0 ml), and sodium azide (269 mg, 4.1 mmol) and then ammonium chloride (275.8 mg, 5.2 mmol) were added, and heated to reflux. After the reaction was complete by TLC (about 5 hrs), water was added to the solution. A solid was precipitated out, which was suctioned, dissolved in EA, and washed with a 3 mol/L sodium hydroxide solution (3×). The aqueous layer was separated, washed twice with a small amount of EA, and adjusted to pH 2 with hydrochloric acid. A solid was precipitated out, which was suctioned and dried, to obtain a pale yellow solid (108 mg). Yield: 13.9%, m.p.>250° C. $^1$H-NMR (300 MHz, DMSO) δ 2.05-2.14 (m, 9H, —CH$_3$), 5.07-5.12 (m, 2H, —NCH$_2$—), 5.81 (s, 1H, —OCH—), 6.67-6.80 (m, 1H, Ar—H), 6.87-6.90 (m, 2H, Ar—H), 6.96-6.99 (m, 2H, Ar—H), 7.03-7.06 (m, 1H, Ar—H), 7.13-7.23 (m, 1H, Ar—H), 7.31-7.33 (m, 1H, Ar—H), 7.45-7.56 (m, 3H, Ar—H), 8.06-8.11 (m, 1H, Ar—H); EI-MS HRMS (ESI): calcd. for C$_{30}$H$_{30}$N$_5$O$_6$S. [M+H]⁺ 588.1807, found 558.1801.

Example 20

(1) Methyl 3-((4-tert-butoxycarbonylamino)naphthalen-1-oxy)-(4-methoxyphenyl) propionate (20-1)

Compound (1-1) (1.8 g, 6.9 mmol) was dissolved in DMF (10 ml), and methyl 4-methoxy-β-bromophenylpropionate (2.0 g, 8.3 mmol) and potassium carbonate (959.4 mg, 6.9 mmol) were added and reacted at room temperature. After the reaction was complete by TLC (about 2 hrs), water was added and then extracted with EA (3×). The organic layers were combined, washed with a saturated ammonium chloride solution (3×) and then a saturated sodium chloride solution (3×), powdered by rotary evaporation to dryness, and separated and purified by column chromatography on silica gel (PE:EA=8:1), to obtain a white solid (1.7 g). Yield: 54.2%, m.p. 212-215° C. $^1$H-NMR (300 MHz, DMSO) δ 1.55 (s, 9H, -Boc), 2.84-2.86 (m, 1H, —CHCH$_2$CO—), 3.09-3.11 (m, 1H, —CHCH$_2$CO—), 3.72 (s, 3H, —COOCH$_3$), 3.87 (s, 3H, —OCH$_3$), 5.65 (s, 1H, —OCH—), 6.48-6.52 (m, 1H, Ar—H), 6.92-6.95 (m, 3H, Ar—H), 7.25-7.28 (m, 2H, Ar—H), 7.59-7.61 (m, 2H, Ar—H), 8.04-8.06 (m, 1H, Ar—H), 8.25-8.28 (m, 1H, Ar—H), 9.18 (s, 1H, —NHCO—); EI-MS m/z: 469 [M+NH$_4$]⁺.

(2) Methyl 3-((2,4,6-trimethylbenzenesulfonamido) naphthalen-1-oxy)-(4-methoxy phenyl) propionate (20-2)

Compound (20-1) (1.7 g, 3.8 mmol) was dissolved in CH$_2$Cl$_2$ (10.0 ml), and CF$_3$COOH (5.0 ml, 67.5 mmol) was added and stirred at room temperature. After the reaction was complete by TLC (about 1 hrs), the reaction solution was adjusted to pH 7 with a saturated Na$_2$CO$_3$ solution and extracted with EA (20 ml×3). The organic layers were combined, washed with a saturated sodium chloride solution (3×), dried over anhydrous sodium sulfate, and rotary evaporated to dryness, to obtain a grey solid which was directly dissolved in THF without further treatment. 2,4,6-trimethylphenylsulfonyl chloride (1.2 g, 5.7 mmol) and then pyridine (606.6 μL, 7.5 mmol) were added and stirred at room temperature. After the reaction was complete by TLC (about 5 hrs), THF was rotary evaporated to dryness, and a small amount of methanol was added to dissolve the oil. A small amount of a dilute hydrochloric acid solution was added. The flask wall was scraped intensely, and there was a solid adhered to the blade. Then, a large amount of dilute hydrochloric acid was added, and a solid was precipitated out, which was suctioned and then slurried in diethyl ether together with the solid adhered to the blade. A solid was precipitated out, which was suctioned to obtain a purple solid (972 mg). Yield: 48.4%, m.p. 221-223° C. $^1$H-NMR (300 MHz, DMSO) δ 2.34 (s, 3H, —CH$_3$), 2.64 (s, 6H, —CH$_3$), 2.84-2.86 (m, 1H, —CHCH$_2$CO—), 3.10-3.12 (m, 1H, —CHCH$_2$CO—), 3.70 (s, 3H, —COOCH$_3$), 3.85 (s, 3H, —OCH$_3$), 5.75 (s, 1H, —OCH—), 6.55-6.57 (m, 1H, Ar—H), 6.88-6.90 (m, 1H, Ar—H), 6.93 (s, 2H, Ar—H), 6.96-6.99 (m, 2H, Ar—H), 7.51-7.61 (m, 4H, Ar—H), 7.97-8.01 (m, 1H, Ar—H), 8.41-8.44 (m, 1H, Ar—H); EI-MS m/z: 556 [M+Na]$^+$.

(3) Methyl 3-((2,4,6-trimethyl-N-(methoxycarbonyl-methyl)benzenesulfonamido) naphthalen-1-oxy)-(4-methoxyphenyl)propionate (20-3)

Compound (20-2) (972.0 mg, 1.8 mmol) was dissolved in DMF (5 ml), and potassium carbonate (377.6 mg, 2.7 mmol) and then methyl bromoacetate (202.7 μL, 2.2 mmol) were added and stirred at room temperature. After the reaction was complete by TLC (about 2 hrs), water was added to the solution, until the solution became cloudy. The solution was adjusted to pH 7 with a saturated NH$_4$Cl solution, and a solid was precipitated out, which was suctioned and dried to obtain a tan solid (684.0 mg). Yield: 62.0%, m.p. 231-232° C. $^1$H-NMR (300 MHz, DMSO) δ 2.28 (s, 3H, —CH$_3$), 2.58 (s, 6H, —CH$_3$), 2.84-2.88 (m, 1H, —CHCH$_2$CO—), 3.09-3.13 (m, 1H, —CHCH$_2$CO—), 3.55-3.58 (m, 3H, —COOCH$_3$), 3.65-3.68 (m, 3H, —COOCH$_3$), 3.81-3.87 (m, 3H, —OCH$_3$), 4.45-4.54 (m, 1H, —NCH$_2$—), 4.74-4.82 (m, 1H, —NCH$_2$—), 5.76 (m, 1H, —OCH—), 6.47-6.50 (m, 1H, Ar—H), 6.88-6.93 (m, 3H, Ar—H), 7.18-7.26 (m, 4H, Ar—H), 7.56-7.58 (m, 2H, Ar—H), 8.06-8.08 (m, 1H, Ar—H), 8.22-8.25 (m, 1H, Ar—H); EI-MS m/z: 606 [M+H]$^+$.

(4) 3-(4-((N-carboxymethyl)-2,4,6-trimethylbenzenesulfonamido)naphthalen-1-yloxy)-(4-methoxyphenyl)propionic acid (I-20)

Compound (20-4) (684.0 mg, 1.1 mmol) was dissolved in methanol (10 ml), and water (5 ml) and then LiOH (500.0 mg, 21.0 mmol) were added and stirred at room temperature. After the reaction was complete by TLC (about 10 hrs), a small amount of water was added to the system until the solid was completely dissolved. The solution was adjusted to pH 4 with a hydrochloric acid solution. The solution became cloudy, and a grey solid was precipitated out, which was stood, suctioned, and dried. 348.0 mg of the grey solid was obtained. Yield: 53.4%, m.p. 240-242° C.

$^1$H-NMR (300 MHz, DMSO) δ 2.34 (m, 3H, —CH$_3$), 2.64 (m, 6H, —CH$_3$), 2.86-2.88 (m, 1H, —CHCH$_2$CO—), 3.11-3.13 (m, 1H, —CHCH$_2$CO—), 3.83-3.85 (m, 3H, —OCH$_3$), 4.28-4.36 (m, 1H, —NCH$_2$—), 4.66-4.74 (m, 1H, —NCH$_2$—), 6.02-6.05 (m, 1H, —OCH—), 6.48-6.49 (m, 1H, Ar—H), 6.89-6.92 (m, 3H, Ar—H), 7.19-7.25 (m, 4H, Ar—H), 7.56-7.58 (m, 2H, Ar—H), 8.06-8.08 (m, 1H, Ar—H), 8.23-8.25 (m, 1H, Ar—H); EI-MS HRMS (ESI): calcd. for C$_{30}$H$_{29}$NNaO$_8$S. [M+Na]$^+$ 600.1806, found 600.1801.

What is claimed is:

1. A compound of Formula (I), or a pharmaceutically acceptable salt thereof:

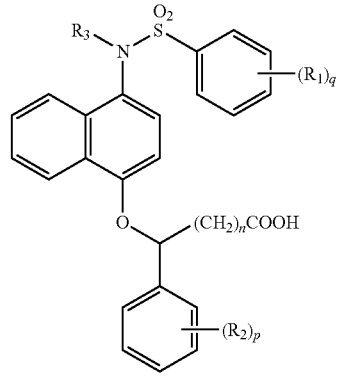

I wherein R$_1$ represents 4-trifluoromethyl, 4-trifluoromethoxy, 4-nitro, 4-hydroxyl, 4-hydroxymethyl, 4-cyano, 4-amino, H, halo, C1-C3 alkyl, C1-C3 alkoxy, C1-C3 alkylamino, or C1-C3 amido;

R$_2$ represents 4-trifluoromethyl, 4-trifluoromethoxy, 4-nitro, 4-hydroxyl, 4-hydroxymethyl, 4-cyano, 4-amino, 4-morpholinylmethoxy, 4-morpholinylethoxy, 4-benzylmethoxy, 4-benzylethoxy, 4-benzylamino, H, halo, C1-C3 alkyl, C1-C3 alkoxy, C1-C3 alkylamino, or C1-C3 amido;

R$_3$ represents H, —CH$_2$COOH,

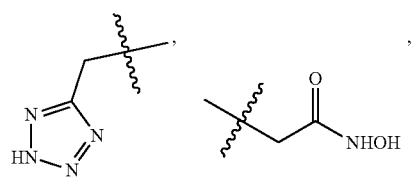

or —CH$_2$CONH$_2$;

p=1-3;
q=1-3; and
n=0-3.

2. The compound according to claim 1 or a pharmaceutically acceptable salt thereof, wherein R$_1$ represents 4-methoxy, 4-bromo, 4-chloro, 4-fluoro, 2,4,6-trimethyl, 4-tert-butyl, 2,4,6-trimethoxy, 4-methyl, 3,4-dimethoxy, 4-acetamido or 4-trifluoromethyl.

3. The compound according to claim 1 or a pharmaceutically acceptable salt thereof, wherein R$_2$ represents 4-methoxy, 4-ethoxy, 4-isopropoxy, 4-fluoro, 4-chloro, 4-bromo, 4-acetamido, 4-trifluoromethyl, 4-hydroxyl, 4-morpholinylmethoxy, 4-morpholinylethoxy, 4-amino, or 4-benzylamino.

4. The compound according to claim 1 or a pharmaceutically acceptable salt thereof, wherein R$_3$ represents —CH$_2$COOH or

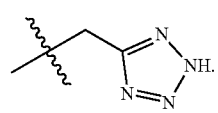 [SMILES: *Cc1nn[nH]n1]

5. The compound according to claim 1 or a pharmaceutically acceptable salt thereof, wherein n represents 0 or 1.

6. The compound according to claim 1 or a pharmaceutically acceptable salt thereof, wherein the pharmaceutically acceptable salt is a sodium, potassium or calcium carboxylate of the compound of Formula (I).

7. A method for preparing the compound according to claim 1, the method comprising:

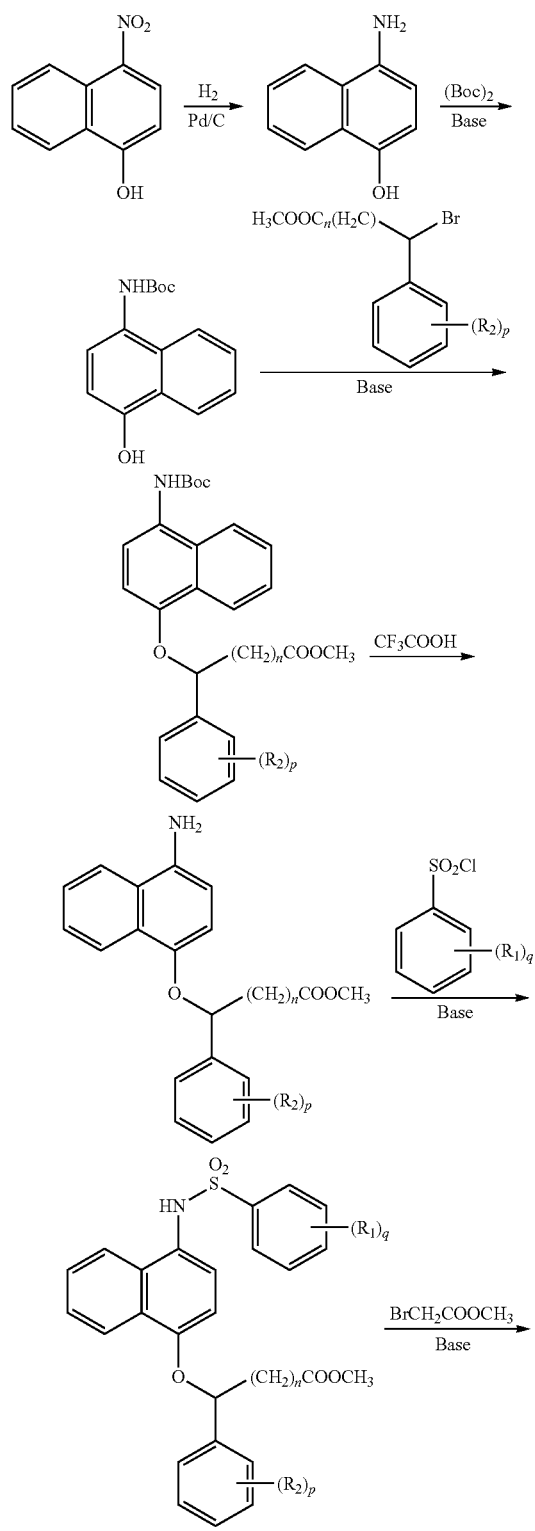

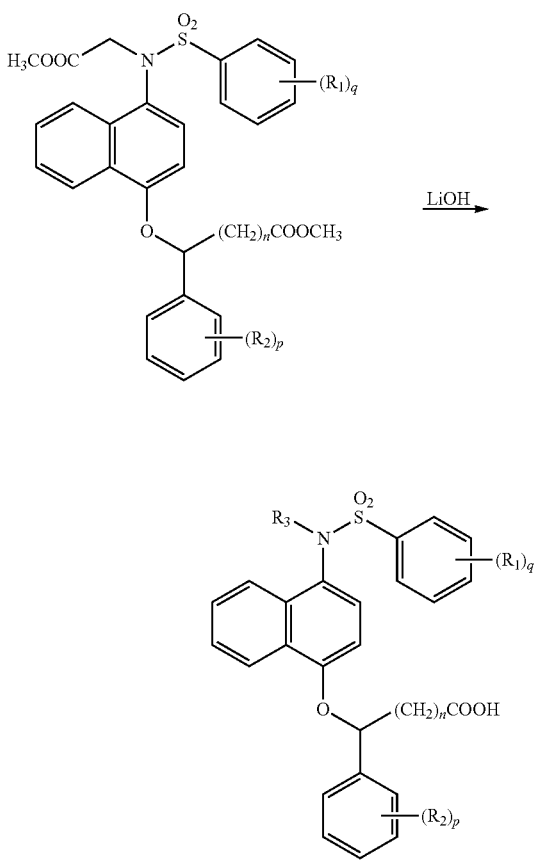

wherein $R_1$, $R_2$, p, q and n are as defined in claim 1, and $R_3$ is $CH_2COOH$.

8. A pharmaceutical composition, comprising the compound according to claim 1 or a pharmaceutically acceptable salt thereof, and a pharmaceutically acceptable carrier.

9. A method for preparing the compound according to claim 1, the method comprising:

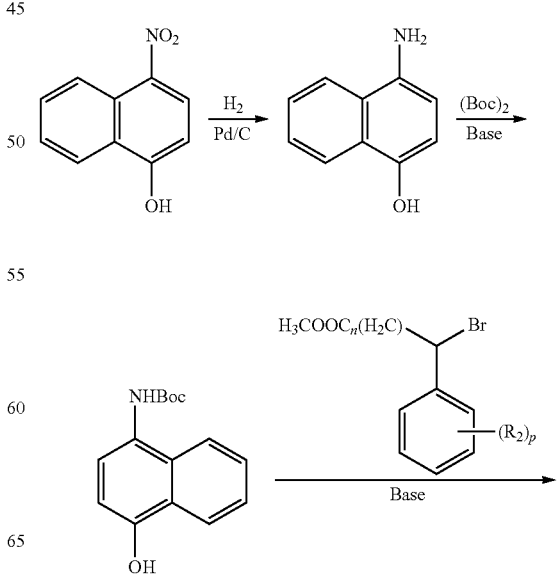

41
-continued
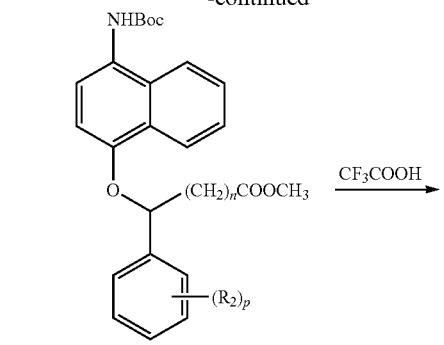
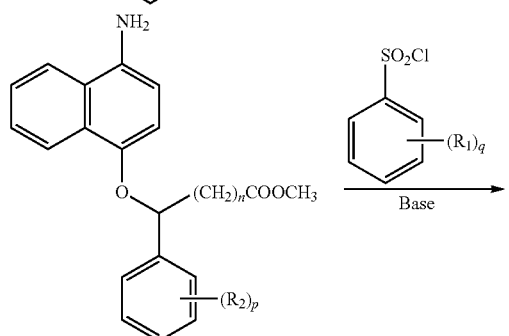
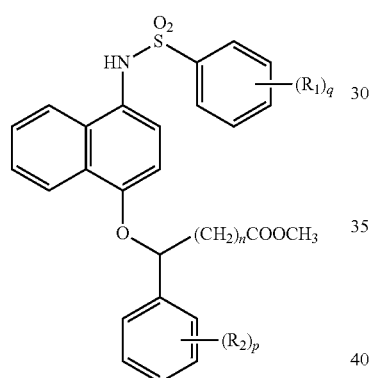
wherein $R_1$, $R_2$, p, q and n are as defined in claim 1, and $R_3$ is H.
10. A method for preparing the compound according to claim 1, the method comprising:
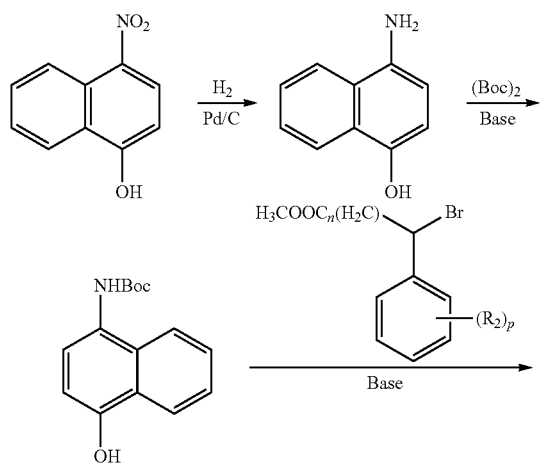
42
-continued
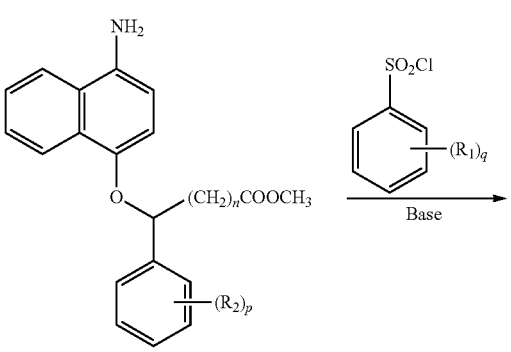
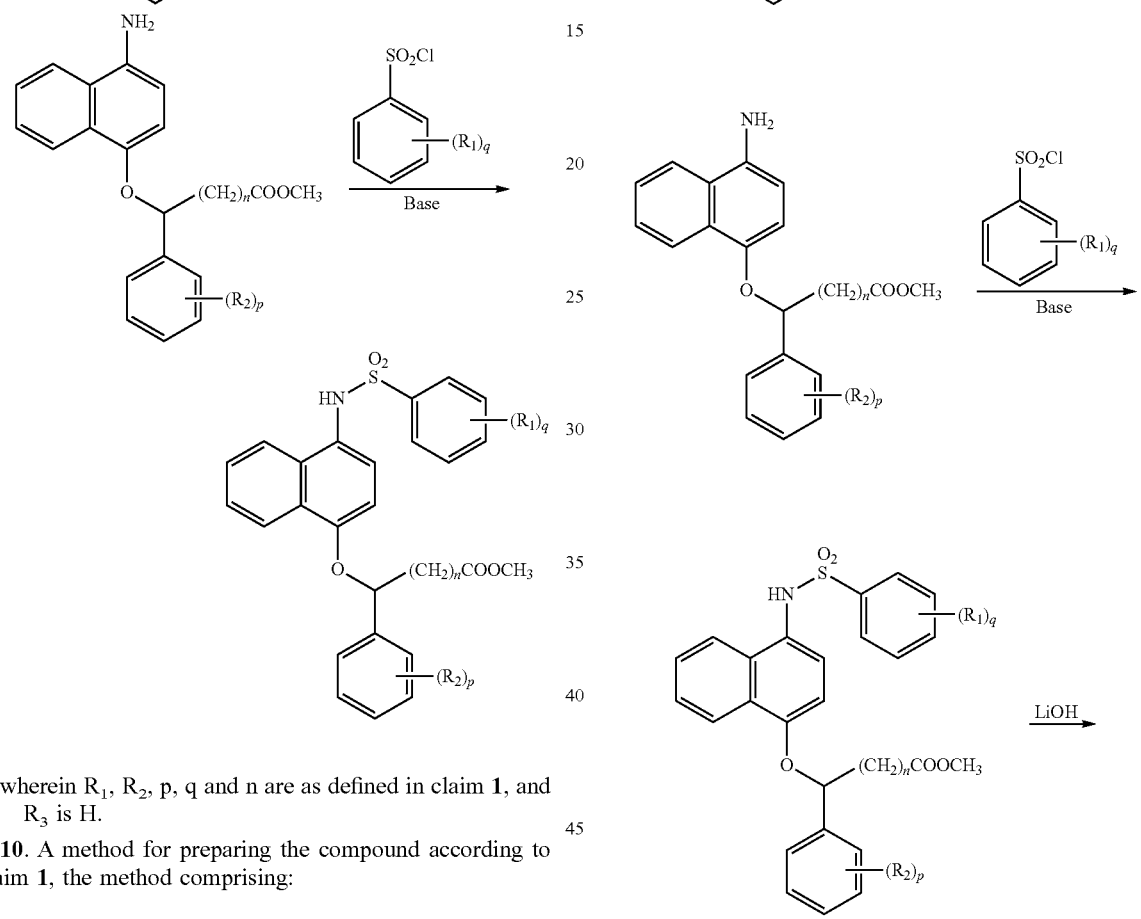

-continued
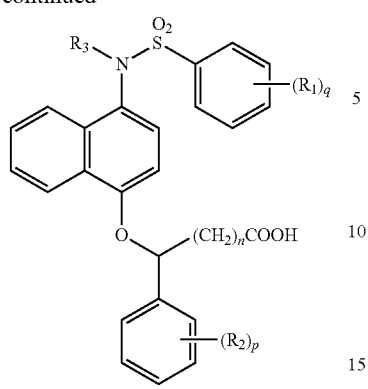
wherein $R_1$, $R_2$, p, q and n are as defined in claim 1, and $R_3$ is
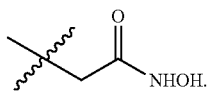
11. A method for preparing the compound according to claim 1, the method comprising:
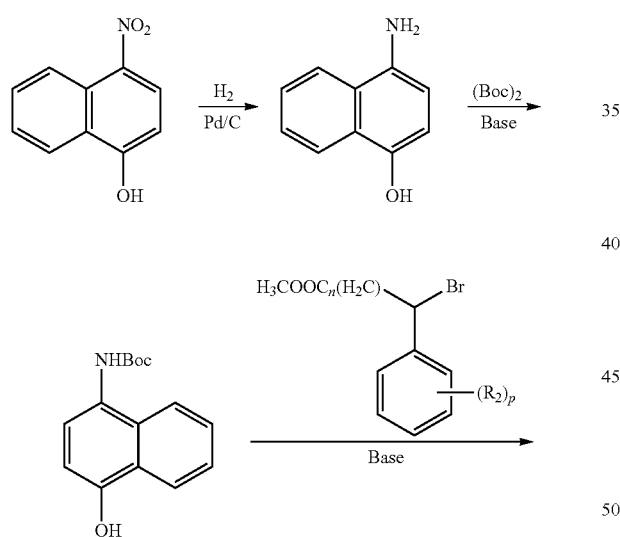
-continued
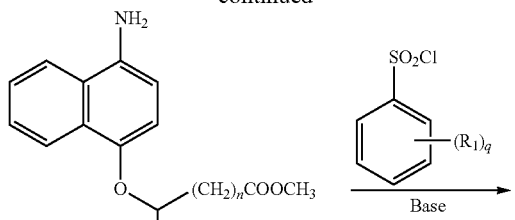
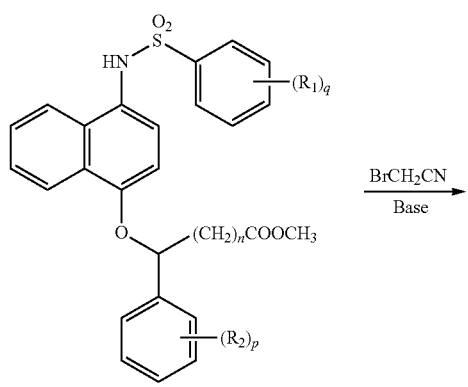
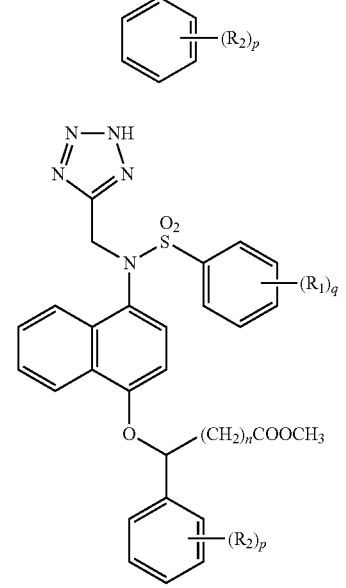

-continued
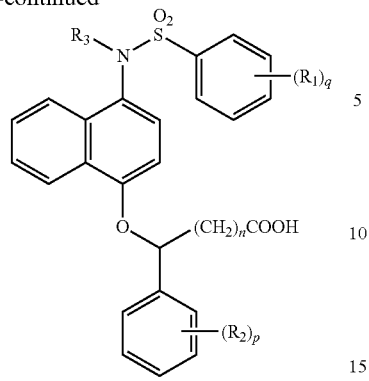
wherein $R_1$, $R_2$, p, q and n are as defined in claim 1, and $R_3$ is
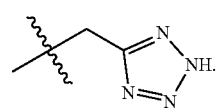 [SMILES: *Cc1nn[nH]n1]
* * * * *